United States Patent
Yuan et al.

(10) Patent No.: US 10,759,859 B2
(45) Date of Patent: Sep. 1, 2020

(54) ANTI-PD-1 ANTIBODIES AND USES THEREOF

(71) Applicant: BPS Bioscience, Inc., San Diego, CA (US)

(72) Inventors: Xiaohui Yuan, San Diego, CA (US); Aaron Snead, San Diego, CA (US); Zhihua Tao, San Diego, CA (US); Kim Skuster, San Diego, CA (US); Colin Cowdrey, San Diego, CA (US); Jonathan Mikolosko, San Diego, CA (US); Andrew Newman, San Diego, CA (US); Henry Zhu, San Diego, CA (US)

(73) Assignee: BPS Bioscience, Inc., San Diego, CA (US)

( * ) Notice: Subject to any disclaimer, the term of this patent is extended or adjusted under 35 U.S.C. 154(b) by 0 days.

(21) Appl. No.: 16/067,469

(22) PCT Filed: Jan. 14, 2017

(86) PCT No.: PCT/US2017/013598
§ 371 (c)(1),
(2) Date: Jun. 29, 2018

(87) PCT Pub. No.: WO2017/124050
PCT Pub. Date: Jul. 20, 2017

(65) Prior Publication Data
US 2019/0016806 A1 Jan. 17, 2019

Related U.S. Application Data

(60) Provisional application No. 62/278,669, filed on Jan. 14, 2016.

(51) Int. Cl.
*C07K 16/28* (2006.01)
*A61K 39/395* (2006.01)

(52) U.S. Cl.
CPC ........ *C07K 16/2818* (2013.01); *A61K 39/395* (2013.01); *C07K 2317/24* (2013.01); *C07K 2317/33* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 2003/0202975 A1 | 10/2003 | Tedder |
| 2003/0235584 A1 | 12/2003 | Kloetzer et al. |
| 2004/0123343 A1 | 6/2004 | La Rosa et al. |
| 2004/0234519 A1 | 11/2004 | Tso et al. |
| 2009/0041783 A1 | 2/2009 | Takayama et al. |
| 2009/0148436 A1 | 6/2009 | LaVallie et al. |
| 2011/0217318 A1 | 9/2011 | Takayama et al. |
| 2011/0223107 A1 | 9/2011 | Tremblay et al. |
| 2011/0229461 A1 | 9/2011 | Tyson |
| 2012/0003235 A1 | 1/2012 | Ranger et al. |
| 2012/0121576 A1 | 5/2012 | Seehra et al. |
| 2013/0110249 A1 | 5/2013 | Schwarz et al. |
| 2013/0288277 A1 | 10/2013 | Kobayashi et al. |
| 2013/0288927 A1 | 10/2013 | Smith et al. |
| 2013/0302349 A1 | 11/2013 | Shriver et al. |
| 2013/0332133 A1 | 12/2013 | Horn et al. |
| 2014/0242085 A1 | 8/2014 | Miyazaki et al. |
| 2015/0010631 A1 | 1/2015 | Getts |
| 2015/0044226 A1 | 2/2015 | Cho et al. |
| 2015/0050283 A1 | 2/2015 | Okano et al. |
| 2015/0125450 A1 | 5/2015 | Goldenberg et al. |

FOREIGN PATENT DOCUMENTS

| | | |
|---|---|---|
| WO | 2006/121168 A1 | 11/2006 |
| WO | 2008/156712 A1 | 12/2008 |
| WO | 2014/194302 A2 | 12/2014 |

OTHER PUBLICATIONS

PCT/US2017/013598 International Search Report and Written Opinion dated May 3, 2017.
UniProtKB/TrEMBL Accession No. A0A0A7PKV7, Mar. 4, 2015 [online]. [Retrieved on Jun. 29, 2018]. Retrieved from the internet ,URL: http://www.uniprot.org/uniprot/A0A0A7PKV7.txt?version=1.
EP17739114.1 Supplementary European Search Report dated Dec. 3, 2018.
Philips et al. "Therapeutic uses of anti-PD-1 and anti-PD-L1 antibodies," International Immunology, Oct. 16, 2014, 27(1)39-46.

*Primary Examiner* — Brad Duffy
(74) *Attorney, Agent, or Firm* — Wagenknecht IP Law Group, PC

(57) ABSTRACT

A subset of humanized anti-PD-1 antibodies that inhibit binding of PD-L1 and PD-L2 to human PD-1. These binding proteins modulate the immune system through the manipulation of the PD-1 signaling pathway to treat immune dysfunctional disorders, including for example cancers.

21 Claims, 6 Drawing Sheets

Specification includes a Sequence Listing.

Human PD-1 Fusion

SEQ ID NO. 17

LDSPDRPWNP PTFSPALLVV TEGDNATFTC SFSNTSESFV LNWYRMSPSN

QTDKLAAFPE DRSQPGQDCR FRVTQLPNGR DFHMSVVRAR RNDSGTYLCG

AISLAPKAQI KESLRAELRV TERRAEVPTA HPSPSPRPAG QFQIEGRMDP

KSCDKTHTCPP CPAPELLGGP SVFLFPPKPK DTLMISRTPE VTCVVVDVSH

EDPEVKFNWY VDGVEVHNAK TKPREEQYNS TYRVVSVLTV LHQDWLNGKE

YKCKVSNKAL PAPIEKTISK AKGQPREPQV YTLPPSREEM TKNQVSLTCL

VKGFYPSDIA VEWESNGQPE NNYKTTPPVL DSDGSFFLYS KLTVDKSRWQ

QGNVFSCSVM HEALHNHYTQ KSLSLSPGK*G GGLNDIFEAQ KIEWHE*

FIG. 5

SEQUENCE LISTING

```
<160> NUMBER OF SEQ ID NOS: 19

<210> SEQ ID NO 1
<211> LENGTH: 6
<212> TYPE: PRT
<213> ORGANISM: mus musculus

<400> SEQUENCE: 1

Thr Ser Gly Tyr Phe Trp
1               5

<210> SEQ ID NO 2
<211> LENGTH: 11
<212> TYPE: PRT
<213> ORGANISM: mus musculus

<400> SEQUENCE: 2

Tyr Ile Ser Tyr Asp Gly Ser Lys Asn Tyr Asn
1               5                   10

<210> SEQ ID NO 3
<211> LENGTH: 8
<212> TYPE: PRT
<213> ORGANISM: mus musculus
```

-continued

<400> SEQUENCE: 3

Gly Gly Leu Pro Val Met Asp Tyr
1               5

<210> SEQ ID NO 4
<211> LENGTH: 17
<212> TYPE: PRT
<213> ORGANISM: mus musculus

<400> SEQUENCE: 4

Lys Ser Ser Gln Ser Leu Leu Asp Asp Asn Asn Gln Lys Asn Tyr Leu
1               5                   10                  15

Ala

<210> SEQ ID NO 5
<211> LENGTH: 7
<212> TYPE: PRT
<213> ORGANISM: mus musculus

<400> SEQUENCE: 5

Phe Ala Ser Thr Arg Glu Ser
1               5

<210> SEQ ID NO 6
<211> LENGTH: 9
<212> TYPE: PRT
<213> ORGANISM: mus musculus

<400> SEQUENCE: 6

Gln Gln His Tyr Thr Thr Pro Tyr Thr
1               5

<210> SEQ ID NO 7
<211> LENGTH: 9
<212> TYPE: PRT
<213> ORGANISM: mus musculus

<400> SEQUENCE: 7

Gln Gln His Tyr Thr Thr Pro Tyr Thr
1               5

<210> SEQ ID NO 8
<211> LENGTH: 11
<212> TYPE: PRT
<213> ORGANISM: mus musculus

<400> SEQUENCE: 8

Trp Ile Gly Tyr Ile Ser Tyr Asp Gly Ser Lys
1               5                   10

<210> SEQ ID NO 9
<211> LENGTH: 5
<212> TYPE: PRT
<213> ORGANISM: mus musculus

<400> SEQUENCE: 9

Leu Pro Val Met Asp
1               5

<210> SEQ ID NO 10
<211> LENGTH: 7
<212> TYPE: PRT
<213> ORGANISM: mus musculus

```
<400> SEQUENCE: 10

Lys Asn Tyr Leu Ala Trp Tyr
1               5

<210> SEQ ID NO 11
<211> LENGTH: 10
<212> TYPE: PRT
<213> ORGANISM: mus musculus

<400> SEQUENCE: 11

Leu Leu Ile Phe Phe Ala Ser Thr Arg Glu
1               5                   10

<210> SEQ ID NO 12
<211> LENGTH: 8
<212> TYPE: PRT
<213> ORGANISM: mus musculus

<400> SEQUENCE: 12

Gln Gln His Tyr Thr Thr Pro Tyr
1               5

<210> SEQ ID NO 13
<211> LENGTH: 117
<212> TYPE: PRT
<213> ORGANISM: artificial sequence
<220> FEATURE:
<223> OTHER INFORMATION: synthetic construct

<400> SEQUENCE: 13

Gln Val Gln Leu Gln Glu Ser Gly Pro Gly Leu Val Lys Pro Ser Gln
1               5                   10                  15

Thr Leu Ser Leu Thr Cys Ser Val Ser Gly Tyr Ser Ile Thr Ser Gly
            20                  25                  30

Tyr Phe Trp Asn Trp Ile Arg Gln Phe Pro Gly Asn Lys Leu Glu Trp
        35                  40                  45

Ile Gly Tyr Ile Ser Tyr Asp Gly Ser Lys Asn Tyr Asn Pro Ser Leu
    50                  55                  60

Lys Asn Arg Val Thr Ile Ile Arg Asp Thr Ser Lys Asn Gln Phe Ser
65                  70                  75                  80

Leu Lys Leu Asn Ser Val Thr Ala Glu Asp Thr Ala Thr Tyr Tyr Cys
                85                  90                  95

Val Arg Gly Gly Leu Pro Val Met Asp Tyr Trp Gly Gln Gly Thr Ser
            100                 105                 110

Val Thr Val Ser Ser
        115

<210> SEQ ID NO 14
<211> LENGTH: 113
<212> TYPE: PRT
<213> ORGANISM: Artificial sequence
<220> FEATURE:
<223> OTHER INFORMATION: synthetic construct

<400> SEQUENCE: 14

Asp Ile Val Met Thr Gln Ser Pro Ser Ser Leu Ala Leu Ser Val Gly
1               5                   10                  15

Glu Lys Ala Thr Ile Gln Cys Lys Ser Ser Gln Ser Leu Leu Asp Asp
            20                  25                  30

Asn Asn Gln Lys Asn Tyr Leu Ala Trp Tyr Gln Gln Lys Pro Gly Gln
        35                  40                  45
```

```
Pro Pro Lys Leu Leu Ile Phe Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Leu Ala Asp Tyr Tyr Cys Gln Gln
                85                  90                  95

His Tyr Thr Thr Pro Tyr Thr Phe Gly Gly Gly Thr Asn Val Glu Ile
            100                 105                 110

Lys

<210> SEQ ID NO 15
<211> LENGTH: 233
<212> TYPE: PRT
<213> ORGANISM: artificial sequence
<220> FEATURE:
<223> OTHER INFORMATION: synthetic construct

<400> SEQUENCE: 15

Gln Val Gln Leu Gln Glu Ser Gly Pro Gly Leu Val Lys Pro Ser Gln
1                   5                   10                  15

Thr Leu Ser Leu Thr Cys Ser Val Ser Gly Tyr Ser Ile Thr Ser Gly
                20                  25                  30

Tyr Phe Trp Asn Trp Ile Arg Gln Phe Pro Gly Asn Lys Leu Glu Trp
            35                  40                  45

Ile Gly Tyr Ile Ser Tyr Asp Gly Ser Lys Asn Tyr Asn Pro Ser Leu
        50                  55                  60

Lys Asn Arg Val Thr Ile Ile Arg Asp Thr Ser Lys Asn Gln Phe Ser
65                  70                  75                  80

Leu Lys Leu Asn Ser Val Thr Ala Glu Asp Thr Ala Thr Tyr Tyr Cys
                85                  90                  95

Val Arg Gly Gly Leu Pro Val Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly
225                 230

<210> SEQ ID NO 16
<211> LENGTH: 220
<212> TYPE: PRT
<213> ORGANISM: Artificial sequence
<220> FEATURE:
<223> OTHER INFORMATION: synthetic construct

<400> SEQUENCE: 16
```

```
Asp Ile Val Met Thr Gln Ser Pro Ser Ser Leu Ala Leu Ser Val Gly
1               5                   10                  15

Glu Lys Ala Thr Ile Gln Cys Lys Ser Ser Gln Ser Leu Leu Asp Asp
            20                  25                  30

Asn Asn Gln Lys Asn Tyr Leu Ala Trp Tyr Gln Lys Pro Gly Gln
        35                  40                  45

Pro Pro Lys Leu Leu Ile Phe Phe Ala Ser Thr Arg Glu Ser Gly Val
50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Leu Ala Asp Tyr Tyr Cys Gln Gln
                85                  90                  95

His Tyr Thr Thr Pro Tyr Thr Phe Gly Gly Gly Thr Asn Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 17
<211> LENGTH: 397
<212> TYPE: PRT
<213> ORGANISM: Artificial sequence
<220> FEATURE:
<223> OTHER INFORMATION: synthetic construct

<400> SEQUENCE: 17

Leu Asp Ser Pro Asp Arg Pro Trp Asn Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Ala Glu Val Pro
        115                 120                 125

Thr Ala His Pro Ser Pro Ser Pro Arg Pro Ala Gly Gln Phe Gln Ile
130                 135                 140
```

```
Glu Gly Arg Met Asp Pro Lys Ser Cys Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Glu Glu Met Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly Lys Gly Gly Gly Leu
    370                 375                 380

Asn Asp Ile Phe Glu Ala Gln Lys Ile Glu Trp His Glu
385                 390                 395
```

<210> SEQ ID NO 18
<211> LENGTH: 699
<212> TYPE: DNA
<213> ORGANISM: Artificial sequence
<220> FEATURE:
<223> OTHER INFORMATION: synthetic construct

<400> SEQUENCE: 18

```
caggtgcagc tgcaggaaag cggcccgggc ctggtgaaac cgagccagac cctgagcctg     60
acctgcagcg tgagcggcta tagcattacc agcggctatt tttggaactg gattcgccag    120
tttccgggca acaaactgga atggattggc tatattagct atgatggcag caaaaactat    180
aacccgagcc tgaaaaaccg cgtgaccatt attcgcgata ccagcaaaaa ccagtttagc    240
ctgaaactga acagcgtgac cgcggaagat accgcgacct attattgcgt gcgcggcggc    300
ctgccggtga tggattattg gggccagggc accagcgtga ccgtgagcag cgcgagcacc    360
aaaggcccga gcgtgtttcc gctggcgccg tgcagccgca gcaccagcga aagcaccgcg    420
gcgctgggct gcctggtgaa agattatttt ccggaaccgg tgaccgtgag ctggaacagc    480
ggcgcgctga ccagcggcgt gcataccttt ccggcggtgc tgcagagcag cggcctgtat    540
agcctgagca gcgtggtgac cgtgccgagc agcagcctgg gcaccaaaac ctatacctgc    600
```

```
aacgtggatc ataaaccgag caacaccaaa gtggataaac gcgtggaaag caaatatggc    660
ccgccgtgcc cgccgtgccc ggcgccggaa tttctgggc                           699

<210> SEQ ID NO 19
<211> LENGTH: 660
<212> TYPE: DNA
<213> ORGANISM: Artificial sequence
<220> FEATURE:
<223> OTHER INFORMATION: synthetic construct

<400> SEQUENCE: 19
gatattgtga tgacccagag cccgagcagc ctggcgctga gcgtgggcga aaaagcgacc     60
attcagtgca aaagcagcca gagcctgctg gatgataaca accagaaaaa ctatctggcg    120
tggtatcagc agaaaccggg ccagccgccg aaactgctga ttttttttgc gagcacccgc    180
gaaagcggcg tgccggatcg ctttattggc agcggcagcg gcaccgattt tacccctgacc  240 attagcagcc tgcaggcgga agatctggcg gattattatt gccagcagca ttataccacc    300
ccgtatacct ttggcggcgg caccaacgtg gaaattaaac gcaccgtggc ggcgccgagc    360
gtgtttattt ttccgccgag cgatgaacag ctgaaaagcg gcaccgcgag cgtggtgtgc    420
ctgctgaaca acttttatcc gcgcgaagcg aaagtgcagt ggaaagtgga taacgcgctg    480
cagagcggca acagccagga aagcgtgacc gaacaggata gcaaagatag cacctatagc    540
ctgagcagca ccctgaccct gagcaaagcg gattatgaaa aacataaagt gtatgcgtgc    600
gaagtgaccc atcagggcct gagcagcccg gtgaccaaaa gctttaaccg cggcgaatgc    660
```

ANTI-PD-1 ANTIBODIES AND USES THEREOF

CROSS REFERENCE TO RELATED APPLICATIONS

This is a U.S. national phase application under 35 USC § 371 of International Patent Application No. PCT/US2017/013598 filed Jan. 14, 2017, which itself claims benefit of priority to U.S. patent application 62/278,669, filed Jan. 14, 2016. Each of the applications referred to in this paragraph are herein incorporated by reference in their entireties.

REFERENCE TO SEQUENCE LISTING SUBMITTED ELECTRONICALLY

The official copy of the sequence listing is submitted electronically via EFS-Web as an ASCII formatted sequence listing with file "BPS_PCT_SEQ_ID" created on Jan. 13, 2017, and having a size of 14 Kilobytes. The sequence listing contained in this ASCII formatted document forms part of the specification and is herein incorporated by reference in its entirety.

BACKGROUND OF THE INVENTION

Lymphocytes exist in a resting state and require stimulation by antigen to proliferate and mount an effective immune response. In the case of T cells, this signal is delivered by major histocompatibility complex (MHC)-bound antigen signaling through T cell receptors (TCR). Full activation of T cells requires the input of various co-stimulatory and co-inhibitory pathways in addition to TCR activation (Croft, M. (2003) Nat. Rev. Immunol. 3:609).

Programmed Death 1, also known as PD-1 and CD279, is a 55 kDa cell surface, co-inhibitory receptor that is expressed mainly by lymphocytes, especially T cells (Blank, C. (2005) Cancer Immunol. Immunother. 54:307). The ligands for PD-1 include PD-L1, also known as B7-H1 and CD274, and PD-L2, also known as B7-DC and CD273. PD-1:PD-L1 or PD-1:PD-L2 interaction results in inhibition of T cell activation, leading to reduced proliferation, pro-inflammatory cytokine secretion, and T cell effector functions, such as T cell cytolysis (Freeman, G. (2000) J. Exp. Med. 192:1027; Latchman, Y. (2001) Nat. Immunol. 2:261; Rodig, N. (2003) Eur. J. Immunol. 33:3117).

In healthy individuals, PD-1 expression is induced by activation of T cells and declines after an immune response successfully eliminates a pathogen (Vibhakar, R. (1997) Exp. Cell Res. 232:25; Zajac, A. (1998) J. Exp. Med. 188:2205). Prolonged antigen stimulation in an unsuccessful immune response in some instances leads to elevated PD-1 expression and an "exhausted" T cell phenotype (Zajac, A. (1998) J. Exp. Med. 188:2205). Knockout of PD-1 in mice is not fatal and in a non-obese mouse diabetic model, knockout of the PD-1 ligand, PD-L1, results in accelerated development of immune mediated diseases (Wang, J. (2005) Proc. Natl. Acad. Sci USA 102:1823). Therefore, its primary role is believed to be in controlling immune responses to prevent the development of autoimmune disorders by down regulating T cell activity.

Many tumors have been shown to have increased expression levels of the ligands (PD-L1 and PD-L2) required for the negative regulation of lymphocytes by PD-1. This is especially true for PD-L1. Squamous cell carcinoma, colon adenocarcinoma, and breast adenocarcinoma have all been shown to have elevated levels of PD-L1 (Brown, J. (2003) J. Immunol. 170:1257). Furthermore, transgenic expression of PD-L1 on tumors in mice leads to increased tumorigenesis and invasion (Iwai, Y. (2002) Proc. Natl. Acad. Sci. USA 99:12293) and tumor growth in mouse melanoma models is abrogated by PD-1 knockout (Iwai, Y. (2005) Int. Immunol. 17:133).

These preclinical studies provide evidence that enhancing T cell function using anti-PD-1 antibodies is a promising treatment for immune dysfunctional disorders, for example cancer. Clinical studies also support this hypothesis. Blockade of immune checkpoint inhibitors, such as through the use of anti-PD-1 antibodies, has demonstrated clinical activity in several types of solid tumors (Brahmer, J. (2010) J. Clin. Oncol. 28:3167; Brahmer J. (2012) N. Engl. J. Med. 366:2455; Hamid, 0. (2013) N. Engl. J. Med. 369:134; Topalian, S. (2014) J. Clin. Oncol. 32:1020; Wolchok, J. (2013) N. Engl. J. Med. 369:122). The first immune checkpoint inhibitor, a fully human immunoglobulin (Ig) G1 monoclonal antibody that blocks cytotoxic T lymphocyte antigen 4 (CTLA4), was approved by the US Food and Drug Administration (FDA) for the treatment of metastatic melanoma in 2011. Three years later, the US FDA approved the first anti-PD-1 antibody for the treatment of advanced melanoma and the first published Phase III trial of PD-1 blockade in the US came in 2015 (Robert, C. (2015) N. Engl. J. Med. 372:320).

While PD-1 appears to be a promising target for the therapeutic treatment, there remains a need to develop improved compositions able to block the interaction of PD-1 with its ligand PD-L1 and PD-L2.

SUMMARY OF THE INVENTION

The invention provides a humanized antibody that specifically binds human PD-1 and interferes with human PD-1 binding to each of PD-L1 and PD-L2. In particular, in one aspect of the invention an antibody or antibody fragment that binds human PD-1 is provided, the antibody or antibody fragment having a heavy chain variable region that include the CDR sequences set forth in SEQ ID NOS. 1-3; and a light chain variable region that includes the CDR sequences set forth in SEQ ID NOS. 4-6.

The antibody or antibody fragment inhibits or reduces PD-1 binding to PD-L1, PD-L2, or PD-L1 and PD-L2. The antibody is preferably in chimeric form and most preferably in a humanized form for use as an active ingredient in a pharmaceutical composition or as a medicament. Preferably, the antibody or antibody fragment binds human PD-1 when human PD-1 has one or more mutations selected from the group consisting of L128A, P130A, I134A, E136A, and K78A.

In some embodiments, the heavy chain variable region has a contact sequence selected from the group consisting of any of the contact sequences set forth in SEQ ID NOS. 7-9, or up to all three contact sequences of SEQ ID NOS. 7-9.

In some embodiments, the heavy chain variable region has an amino acid sequence that has at least 85% sequence identity to SEQ ID NO. 13, or at least 90% sequence identity to SEQ ID NO. 13. In further embodiments, the heavy chain variable region has an amino acid sequence having at least 95% sequence identity to SEQ ID NO. 13, or at least 99% sequence identity to SEQ ID NO. 13. In still further embodiments, the heavy chain variable region has the amino acid sequence set forth in SEQ ID NO. 13.

The light chain variable region can also have a contact sequence selected from the group consisting of any of the contact sequences set forth in SEQ ID NOS. 10-12, or up to all three contact sequences of SEQ ID NOS. 10-12.

In some embodiments the light chain variable region has an amino acid sequence with at least 85% sequence identity to SEQ ID NO. 14, or at least 90% sequence identity to SEQ ID NO. 14. In further embodiments, the light chain variable region has an amino acid sequence with at least 95% sequence identity to SEQ ID NO. 14, or at least 99% sequence identity to SEQ ID NO. 14. In still further embodiments, the light chain variable region has the amino acid sequence set forth in SEQ ID NO. 14.

In a related embodiment the heavy chain variable region has the contact sequences set forth in SEQ ID NOS. 7-9 and the light chain variable region has the contact sequences set forth in SEQ ID NOS. 10-12.

In a related aspect, an antibody or antibody fragment capable of binding human PD-1 is provided, which includes: a heavy chain variable region having at least 85% sequence identity to the amino acid sequence set forth in SEQ ID NO: 13, the heavy chain variable region also having the three CDR sequences set forth in SEQ ID NOS. 1-3 and the three contact sequences set forth in SEQ ID NOS. 7-9; and a light chain region variable region having at least 85% sequence identity to the amino acid sequence set forth in SEQ ID NO: 14, the light chain variable region also having the three CDR sequences set forth in SEQ ID NOS. 4-6 and three contact sequences of SEQ ID NOS. 10-12.

In some embodiments, the heavy chain variable region has at least 90% sequence identity to the amino acid sequence of SEQ ID NO. 13 and the light chain variable region has at least 90% sequence identity to the amino acid sequence of SEQ ID NO. 14. In further embodiments, the heavy chain variable region has at least 95% sequence identity to the amino acid sequence of SEQ ID NO. 13 and the light chain variable region has at least 95% sequence identity to the amino acid sequence of SEQ ID NO. 14. In still further embodiments, the heavy chain variable region has at least 99% sequence identity to the amino acid sequence of SEQ ID NO. 13 and the light chain variable region has at least 99% sequence identity to the amino acid sequence of SEQ ID NO. 14. In still further embodiments the heavy chain variable region has the amino acid sequence of SEQ ID NO. 13 and the light chain variable region has the amino acid sequence of SEQ ID NO. 14.

Each of the antibodies of the various aspects can be provided in isolated form. When adapted for use in therapeutics, the each of the antibodies can be provided with a pharmaceutically acceptable carrier.

In other related aspects of the invention, a nucleic acid sequence encoding any of the anti-PD1 antibodies or antibody fragments can be provided.

In still another related aspect, a method of interfering with the interaction of PD-L1 with human PD-1 is provided, which includes providing a sample including human PD-1; contacting the PD-1 with one of the anti-PD1 antibodies or antibody fragments; and exposing the PD-1 to PD-L1.

In still another related aspect, a method of interfering with the interaction of PD-L2 with human PD-1 is provided, which includes providing a sample of human PD-1; contacting the PD-1 with one of the anti-PD1 antibodies or antibody fragments; and exposing the PD-1 to PD-L2.

In still another related aspect, a method of interfering with the interaction of PD-L1 and PD-L2 with human PD-1 is provided, which includes: providing a sample of human PD-1; contacting the PD-1 with one of the anti-PD1 antibodies or antibody fragments; and exposing the PD-1 to PD-L1 and PD-L2.

In still another related aspect, a method of reducing PD-1 signaling in a cell is provided, which includes providing a cell expressing human PD-1; contacting the cell with one of the anti-PD1 antibodies or antibody fragments; and exposing the cell to PD-L1.

In still another related aspect, a method of reducing PD-1 signaling in a cell is provided, which includes providing a cell expressing human PD-1; contacting the cell with one of the anti-PD1 antibodies or antibody fragments; and exposing the cell to PD-L2.

In still another related aspect, a method of reducing PD-1 signaling in a cell is provided, which includes providing a cell expressing human PD-1; contacting the cell with one of the anti-PD1 antibodies or antibody fragments; and exposing the cell to PD-L1 and PD-L2.

BRIEF DESCRIPTION OF THE DRAWINGS

FIG. 5 depicts a human PD-1 fusion protein to test binding with anti-PD-1 antibodies.

DETAILED DESCRIPTION OF PREFERRED EMBODIMENTS

Figure 1A:
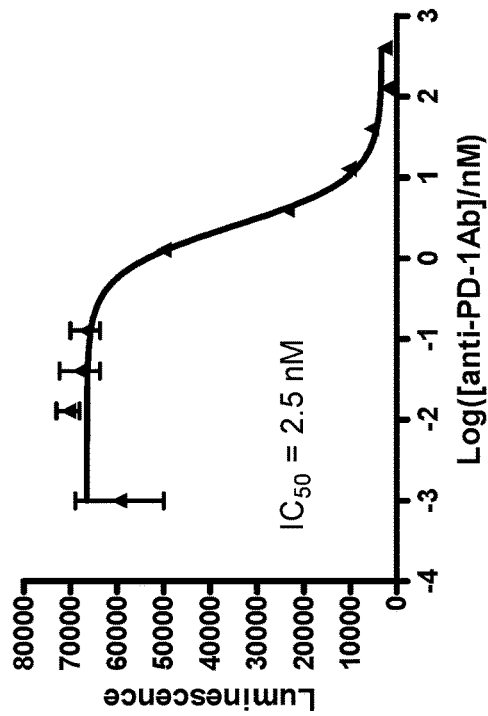
FIG. 1A and FIG. 1B are a series of graphs depicting inhibition of human PD-1:PD-L1 interaction with BPS hAb-10D3 (FIG. 1A) over a series of different concentrations compared to positive control (FIG. 1B).

The invention provides anti-human PD-1 antibodies and antibody fragments thereof, which are termed anti-PD-1 antibodies collectively for brevity. These antibodies inhibit or interfere with the interaction between human PD-1 with PD-L1, human PD-1 with PD-L2, or both PD-1 with PD-L1 and with PD-L2. The anti-PD-1 antibodies, in some embodiments, act as antagonists to PD-1 activity, thereby attenuating or blocking PD-1 inhibitory signals that negatively modulate T cell activation. An anti-PD-1 antibody with the capability of blocking PD-1 inhibitory signals has uses in a variety of clinical applications, including, for example, enhancing host anti-microbial immunity when treating persistent infections, nullifying tumor immune evasion to enhance host anti-cancer immunity, and providing adjuvant-like properties when combined with vaccines for induction of cellular immune responses.

A. Definitions

Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the Internet can come and go, but equivalent information can be found by searching the Internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "ADVANCED ORGANIC CHEMISTRY 4$^{th}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein as such may vary. It is also to be understood that the terminology used herein is for the purpose of describing particular embodiments only, and is not intended to limit the scope of the methods, compounds, compositions described herein.

The terms "treat," "treating" or "treatment" with the anti-PD1 antibody includes alleviating, abating or ameliorating a disease, disorder or condition symptoms, preventing additional symptoms, ameliorating or preventing the underlying metabolic causes of symptoms, inhibiting the disease, disorder, or condition, e.g., arresting the development of the disease, disorder or condition, relieving the disease, disorder or condition, causing regression of the disease, disorder or condition, relieving a condition caused by the disease, disorder or condition, or stopping the symptoms of the disease, disorder or condition. The terms "treat," "treating" or "treatment", include, but are not limited to, prophylactic and/or therapeutic treatments.

The term "acceptable" or "pharmaceutically acceptable", with respect to a formulations of the anti-PD-1 antibodies, refers to ingredients having no persistent detrimental effect on the general health of the subject being treated or does not abrogate the biological activity or properties of one or more anti-PD-1 antibodies described herein, and is relatively nontoxic.

The term "amelioration" of the symptoms of a particular disease, disorder or condition by administration of the anti-PD-1 antibody or pharmaceutical composition refers to any lessening of severity, delay in onset, slowing of progression, or shortening of duration, whether permanent or temporary, lasting or transient that can be attributed to or associated with administration of the anti-PD-1 antibody or a pharmaceutical composition including an anti-PD-1 antibody.

The term "pharmaceutical combination" as used herein, means a product that results from the mixing or combining of more than one active ingredient (e.g. anti-PD1 antibody) and includes both fixed and non-fixed combinations of the active ingredients. The term "fixed combination" means that one active ingredient (e.g. an anti-PD-1 antibody) and a co-agent are both administered to a patient simultaneously in the form of a single entity or dosage. The term "non-fixed combination" means that one active ingredient (e.g. an anti-PD-1 antibody) and a co-agent are administered to a patient as separate entities either simultaneously, concurrently or sequentially with no specific intervening time limits, wherein such administration provides effective levels of the two agents in the body of the patient. The latter also applies to cocktail therapy, e.g. the administration of three or more active ingredients.

The term "pharmaceutical composition" as used herein refers to one or more anti-PD-1 antibodies with one or more other chemical components, such as carriers, stabilizers, diluents, dispersing agents, suspending agents, thickening agents, and/or excipients. The pharmaceutical composition facilitates administration of an anti-PD-1 antibody to an organism. Multiple techniques of administering an anti-PD-1 antibody exist in the art including, but not limited to: topical, ophthalmic, intraocular, periocular, intravenous, oral, aerosol, parenteral, and administration.

The term "carrier," as used herein, refers to relatively nontoxic chemical compounds or agents that facilitate the incorporation of an agent of interest (e.g., an anti-PD-1 antibody) into cells or tissues.

The term "diluent" refers to chemical compounds that are used to dilute the agent of interest (e.g., an anti-PD-1 antibody) prior to delivery. Diluents can also be used to stabilize agents because they can provide a more stable environment. Salts dissolved in buffered solutions (which also can provide pH control or maintenance) are utilized as diluents in the art, including, but not limited to a phosphate buffered saline solution.

The terms "co-administration" or the like, are meant to encompass administration of the selected agents (e.g., an anti-PD-1 antibody or composition thereof and a co-agent) to a single patient, and are intended to include treatment regimens in which the agents are administered by the same or different route of administration or at the same or different time.

The terms "effective amount" or "therapeutically effective amount," refer to a sufficient amount an anti-PD-1 antibody, agent, combination or pharmaceutical composition described herein administered which will relieve to some extent one or more of the symptoms of the disease, disorder or condition being treated. The result can be reduction and/or alleviation of the signs, symptoms, or causes of a disease, or any other desired alteration of a biological system. For example, an "effective amount" for therapeutic uses is the amount of the anti-PD-1 antibody, agent, combination or pharmaceutical composition required to provide a desired pharmacologic effect, therapeutic improvement, or clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. It is understood that "an effect amount" can vary from subject to subject due to variation in metabolism of an anti-PD-1 antibody, genetics, combination, or pharmaceutical composition, age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The term "prophylactically effective amount," refers that amount of an anti-PD-1 antibody, compound, agent, combination or pharmaceutical composition described herein applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The term "subject" or "patient" as used herein, refers to an animal, which is the object of treatment, observation or experiment. By way of example only, a subject may be, but is not limited to, a mammal including, but not limited to, a human.

The terms "enhance" or "enhancing" means to increase or prolong either in potency or duration a desired effect. By way of example, "enhancing" the effect of therapeutic agents singly or in combination refers to the ability to increase or prolong, either in potency, duration and/or magnitude, the effect of the agents on the treatment of a disease, disorder or condition. When used in a patient, amounts effective for this use will depend on the severity and course of the disease, disorder or condition, previous therapy, the patient's health status and response to the drugs, and the judgment of the treating physician.

The term "modulate," means to interact with a target (e.g., PD-1) either directly or indirectly so as to alter the activity of the target, including, by way of example only, to enhance the activity of the target, to inhibit or antagonize the activity of the target, to limit the activity of the target, or to extend the activity of the target. In some embodiments, anti-PD-1 antibodies and pharmaceutical compositions described herein can modulate the activity of one or more respective targets (e.g., one or more anti-PD-1 antibody). In some embodiments, an anti-PD-1 antibody described herein modulates (e.g., decreases) the activity of PD-1 on a cell (e.g., a T cell), resulting, e.g., in T cell activation and increase T cell effector functions.

As used herein, the term "target" refers to a biological molecule (e.g., a target protein or protein complex), such as PD-1, or a portion of a biological molecule capable of being bound by a selective binding agent (e.g., an anti-PD-1 antibody) or pharmaceutical composition described herein. As used herein, the term "non-target" refers to a biological molecule or a portion of a biological molecule that is not selectively bound by a selective binding agent or pharmaceutical composition described herein.

The term "target activity" or "cell response" refers to a biological activity capable of being modulated by an anti-PD-1 antibody or any cellular response that results from the binding of an anti-PD-1 antibody to a PD-1 receptor. Certain exemplary target activities and cell responses include, but are not limited to, binding affinity, signal transduction, gene expression, cell migration, cell proliferation, cell differentiation, cell-mediated cytotoxicity, and amelioration of one or more symptoms associated with cancer.

The term "amino acid" refers to the molecules composed of terminal amine and carboxylic acid functional groups with a carbon atom between the terminal amine and carboxylic acid functional groups sometimes containing a side chain functional group attached to the carbon atom (e.g. a methoxy functional group, which forms the amino acid serine). Typically, amino acids are classified as natural and non-natural. Examples of natural amino acids include glycine, alanine, valine, leucine, isoleucine, proline, phenylananine, tyrosine, tryptophan, serine, threonine, cysteine, methionine, asparagine, glutamine, lysine, arginine, histidine, aspartate, and glutamate, among others. Examples of non-natural amino acids include L-3,4-dihydroxyphenylalanine, 2-aminobutyric acid, dehydralanine, g-carboxyglutamic acid, carnitine, gamma-aminobutyric acid, hydroxyproline, and selenomethionine, among others. In the context of this specification it should be appreciated that the amino acids may be the L—optical isomer or the D—optical isomer

B. Anti-PD-1 Antibodies

Figure 6:
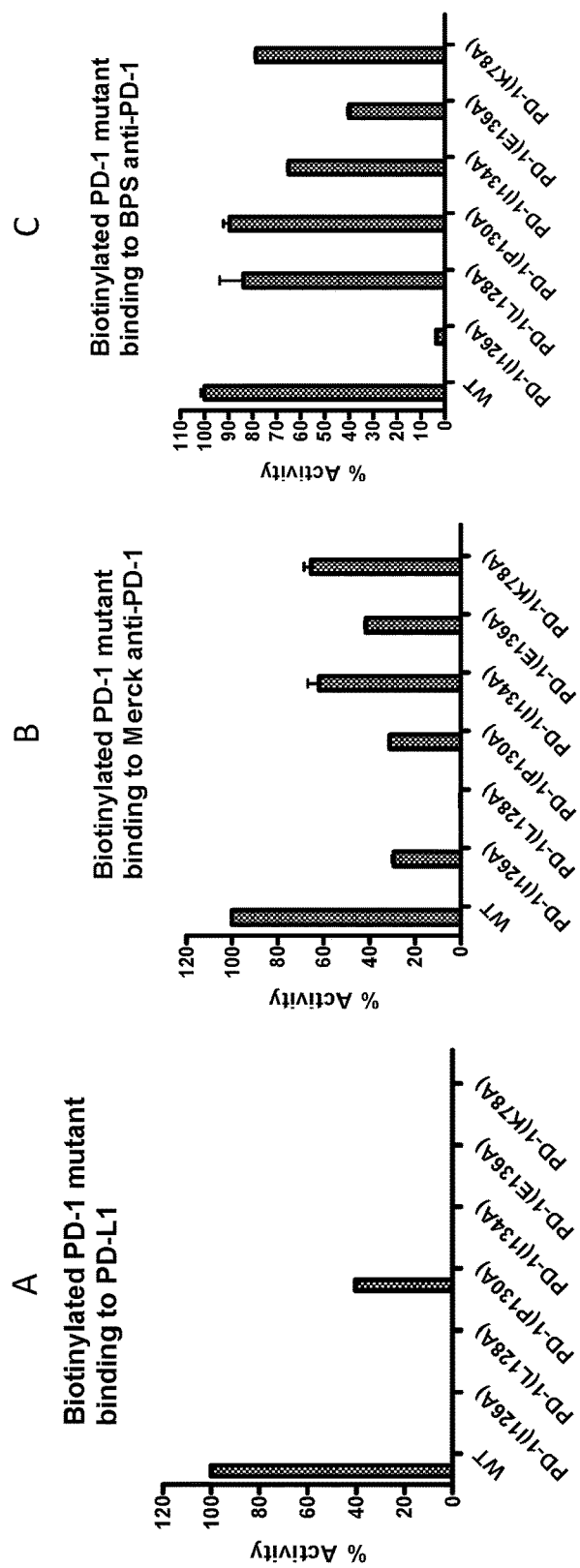
FIG. 6 provides a series of graphs comparing the binding of a commercially available Merck ant-PD-1 antibody (CAT#71120) to BPS hAb-10D3 over various mutations in human PD-1, which confirms different amino acid groups on human PD-1 are involved in binding interactions.

The invention provides antibodies, which also refers to antibody fragments, that bind human PD-1. BPS Antibody 10D3 (humanized form also referred to as hAb-10D3) demonstrates a high specificity for PD-1 and an ability to effectively inhibit or reduce PD-1 signaling. As shown in FIGS. 1-4, Clone hAb10D3 interferes with both PD-1:PD-L1 binding and PD-1:PD-L2 binding. Furthermore, mutation analysis of PD-1 demonstrated clone h-Ab10D3 recognizes a different epitope compared to Merck's anti-PD1 (CAT#71120) (FIG. 6). Sequence data of the key regions of clone huAb-10D3 is shown in TABLE 1:

TABLE 1

SEQUENCE DATA OF hAb-10D3

| SEQ. ID | DESCRIPTION | SEQUENCE |
| --- | --- | --- |
| 1 | CDR of antibody Heavy Chain Variable Region | TSGYFW |
| 2 | CDR of antibody Heavy Chain Variable Region | YISYDGSKNYN |
| 3 | CDR of antibody Heavy Chain Variable Region | GGLPVMDY |
| 4 | CDR of antibody Light Chain Variable Region | KSSQSLLDDNNQKNYLA |

TABLE 1-continued

SEQUENCE DATA OF hAb-10D3

| SEQ. ID | DESCRIPTION | SEQUENCE |
|---|---|---|
| 5 | CDR of antibody Light Chain Variable Region | FASTRES |
| 6 | CDR of antibody Light Chain Variable Region | QQHYTTPYT |
| 7 | Contact Region of antibody Heavy Chain Variable Region | ITSGYFWN |
| 8 | Contact Region of antibody Heavy Chain Variable Region | WIGYISYDGSK |
| 9 | Contact Region of antibody Heavy Chain Variable Region | LPVMD |
| 10 | Contact Region of antibody Light Chain Variable Region | KNYLAWY |
| 11 | Contact Region of antibody Light Chain Variable Region | LLIFFASTRE |
| 12 | Contact Region of antibody Light Chain Variable Region | QQHYTTPY |
| 13 | Heavy Chain Variable Region | QVQLQESGPGLVKPSQTLSLTCSVSGYS ITSGYFWNWIRQFPGNKLEWIGYISYDG SKNYNPSLKNRVTIIRDTSKNQFSLKLN SVTAEDTATYYCVRGGLPVMDYWGQ GTSVTVSS |
| 14 | Light Chain Variable Region | DIVMTQSPSSLALSVGEKATIQCKSSQS LLDDNNQKNYLAWYQQKPGQPPKLLI FFASTRESGVPDRFIGSGSGTDFTLTISS LQAEDLADYYCQQHYTTPYTFGGGTN VEIK |
| 15 | Heavy Chain F(ab) | QVQLQESGPGLVKPSQTLSLTCSVSGY SITSGYFWNWIRQFPGNKLEWIGYISY DGSKNYNPSLKNRVTIIRDTSKNQFSL KLNSVTAEDTATYYCVRGGLPVMDY WGQGTSVTVSSASTKGPSVFPLAPCSR STSESTAALGCLVKDYFPEPVTVSWN SGALTSGVHTFPAVLQSSGLYSLSSVV TVPSSSLGTKTYTCNVDHKPSNTKVD KRVESKYGPPCPPCPAPEFLG |
| 16 | Light Chain F(ab) | DIVMTQSPSSLALSVGEKATIQCKSSQ SLLDDNNQKNYLAWYQQKPGQPPKL LIFFASTRESGVPDRFIGSGSGTDFTLT ISSLQAEDLADYYCQQHYTTPYTFGG GTNVEIKRTVAAPSVFIFPPSDEQLKS GTASVVCLLNNFYPREAKVQWKVD NALQSGNSQESVTEQDSKDSTYSLSS TLTLSKADYEKHKVYACEVTHQGLS SPVTKSFNRGEC |
| 18 | Heavy Chain F(ab) reverse translation | caggtgcagctgcaggaaagcggccccgggcct ggtgaaaccgagccagaccctgagcctgacct gcagcgtgagcggctatagcattaccagcggc tattttggaactggattcgccagtttccggg caacaaactggaatggattggctatattagct atgatggcagcaaaaactataacccgagcctg aaaaaccgcgtgaccattattcgcgataccag caaaaaccagtttagcctgaaactgaacagcg tgaccgcggaagataccgcgacctattattgc gtgcgcggcggcctgccggtgatggattattg gggccagggcaccagcgtgaccgtgagcagcg cgagcaccaaaggcccgagcgtgtttccgctg gcgccgtgcagccgcagcaccagcgaaagcac cgcggcgctgggctgcctggtgaaagattatt ttccggaaccggtgaccgtgagctggaacagc ggcgcgctgaccagcggcgtgcatacctttcc ggcggtgctgcagagcagcggcctgtatagcc |
| 19 | Light Chain F(ab) reverse translation | tgagcagcgtggtgaccgtgccgagcagcagc ctgggcaccaaaacctatacctgcaacgtgga tcataaaccgagcaacaccaaagtggataaac gcgtggaaagcaaatatggcccgccgtgcccg ccgtgcccggcgccggaatttctggc gatattgtgatgacccagagcccgagcag ctggcgctgagcgtgggcgaaaaagcga ccattcagtgcaaaagcagccagagcctg ctggatgataacaaccagaaaaactatct ggcgtggtatcagcagaaaccgggccagc cgccgaaactgctgattttttttgcgagc acccgcgaaagcggcgtgccggatcgctt tattggcagcggcagcggcaccgattta ccctgaccattagcagcctgcaggcggaa gatctggcgattattgccagcagca ttataccaccccgtataccttttggcgcg gcaccaacgtggaaattaaacgcaccgtg gcggcgccgagcgtgtttatttttccgcc gagcgatgaacagctgaaaagcggcaccg cgagcgtggtgtgcctgctgaacaactt tatccgcgcgaagcgaaagtgcagtggaa agtggataacgcgctgcagagcggcaaca gccaggaaagcgtgaccgaacaggatagc aaagatagcacctatagcctgagcagcac cctgaccctgagcaaagcggattatgaaa aacataaagtgtatgcgtgcgaagtgacc catcagggcctgagcagcccggtgaccaa aagctttaaccgcggcgaatgc |

Accordingly, the invention provides an antibody that binds human PD-1. In particular, the antibody has a heavy chain variable region having the CDR sequences set forth in SEQ ID NOS. 1-3; and a light chain variable region having the CDR sequences set forth in SEQ ID NOS. 4-6. In further embodiments the heavy chain variable region has a contact sequence selected from the group consisting of any of the contact sequences set forth in SEQ ID NOS. 7-9, optionally all three contact sequences of SEQ ID NOS. 7-9.

In some embodiments, the heavy chain variable region has an amino acid sequence with at least 85% sequence identity to SEQ ID NO. 13, optionally at least 90% sequence identity to SEQ ID NO. 13. In further embodiments, the heavy chain variable region has an amino acid sequence having at least 95% sequence identity to SEQ ID NO. 13, optionally at least 99% sequence identity to SEQ ID NO. 13. Humanized anti-PD-1 antibody hAb-10D3 has a heavy chain variable region with the amino acid sequence set forth in SEQ ID NO. 13.

In some embodiments the anti-PD-1 antibody has a light chain variable region having a contact sequence selected from the group consisting of any of the contact sequences set forth in SEQ ID NOS. 10-12, optionally all three contact sequences of SEQ ID NOS. 10-12. Preferably, the light chain variable region has an amino acid sequence having at least 85% sequence identity to SEQ ID NO. 14, optionally at least 90% sequence identity to SEQ ID NO. 14. In further embodiments, the light chain variable region has an amino acid sequence having at least 95% sequence identity to SEQ ID NO. 14, optionally at least 99% sequence identity to SEQ ID NO. 14. Humanized clone hAb-10D3 has a light chain variable region including the amino acid sequence set forth in SEQ ID NO. 14.

While the heavy chain variable region and light chain variable region may be combined with other light chain variable regions and other heavy chain variable regions respectively, so long as PD-1 binding can be maintained, in some embodiments, the anti-human PD-1 antibody includes a heavy chain variable region having at least 85% sequence identity to the amino acid sequence set forth in SEQ ID NO: 13, the heavy chain variable region further having three CDR sequences set forth in SEQ ID NOS. 1-3 and three contact sequences set forth in SEQ ID NOS. 7-9; and a light chain region variable region having at least 85% sequence identity to the amino acid sequence set forth in SEQ ID NO: 14, the light chain variable region also having the three CDR sequences set forth in SEQ ID NOS. 4-6 and the three contact sequences of SEQ ID NOS. 10-12.

In further embodiments, the heavy chain variable region has at least 90% sequence identity to the amino acid sequence of SEQ ID NO. 13 and the light chain variable region has at least 90% sequence identity to the amino acid sequence of SEQ ID NO. 14. In still further embodiments, the heavy chain variable region has at least 95% sequence identity to the amino acid sequence of SEQ ID NO. 13 and the light chain variable region has at least 95% sequence identity to the amino acid sequence of SEQ ID NO. 14. In still further embodiments, the heavy chain variable region has at least 99% sequence identity to the amino acid sequence of SEQ ID NO. 13 and the light chain variable region has at least 99% sequence identity to the amino acid sequence of SEQ ID NO. 14. In humanized clone hAb-10D3 the heavy chain variable region has the amino acid sequence of SEQ ID NO. 13 and the light chain variable region has the amino acid sequence of SEQ ID NO. 14.

As indicated above, the invention encompasses variations in sequence around the CDRs within a percent sequence identity. The term "percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical. Likewise, 85% amino acid sequence identity means that 85% of the amino acids in two optimally aligned polypeptide sequences are identical; and 90%, 95%, and 99% amino acid sequence identity means that 90%, 95%, and 99% respectively of the amino acids in two optimally aligned polypeptide sequences are identical.

Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in "Atlas of Protein Sequence and Structure", M. O. Dayhoff et., Suppl. 3:353-358, National Biomedical Research Foundation, Washington, D.C., which adapts the local homology algorithm of Smith and Waterman (1981) Advances in Appl. Math. 2:482-489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters 5 recommended by the manufacturer and described in the Wisconsin Sequence Analysis Package referred to above. An example of an algorithm that is suitable for determining sequence similarity is the BLAST algorithm, which is described in Altschul, et al., J. Mol. Biol. 215:403-410 (1990). Software for performing BLAST analyses is publicly available through the National Center for Biotechnology Information. Likewise, computer programs for determining percent homology are also readily available.

Variations in sequence identity are permitted outside of the CDRs because not all amino acid sequence within the heavy and light variable regions are required for binding PD-1. In particular regions outside of CDRs or CDRs and contact sites, such as framework regions, may be mutated without losing PD-1 binding capability. Still further, framework regions may be further mutated and thus vary in sequences when adapting the CDRs for the treatment of different species. Mutations or variations can be described by use of the following nomenclature: position (#); substituted amino acid residue(s). According to this nomenclature, the substitution of, for instance, an alanine residue for a glycine residue at position can be indicated as A#G, where # represents the position. When an amino acid residue at a given position is substituted with two or more alternative amino acid residues, these residues are separated by a comma or a slash. For example, substitution of alanine with either glycine or glutamic acid can be indicated as #G/E, or #G, #E. The deletion of alanine in the same position can be shown as Ala#* or A#* or *#Ala or *#A, where # refers to the position of the amino acid. Multiple mutations are separated by a plus sign or a slash. For example, two mutations in positions (each indicated by "#") substituting alanine and glutamic acid for glycine and serine, respectively, are indicated as A#G+E#S or A#G/E#S. When an amino acid residue at a given position # is substituted with two or more alternative amino acid residues, these residues are separated by a comma or a slash. For example, substitution of alanine at a position # with either glycine or glutamic acid is indicated as A#G,E or A#G/E, or A#G, A#E. When a position # suitable for modification is identified herein without any specific modification being suggested, it is to be understood that any amino acid residue may be substituted for the amino acid residue present in the position. Thus, for instance, when a modification of an alanine at a position # is mentioned but not specified, it is to be understood that the alanine may be deleted or substituted for any other amino acid residue (i.e. any one of R, N, D, C, Q, E, G, H, I, L, K, M, F, P, S, T, W, Y and V).

Substitutions outside of the CDRs or CDRs and contact sequences can be conservative mutations or conservative substitutions. The terms "conservative mutation", or "conservative substitution", respectively, refer to an amino acid mutation that a person skilled in the art would consider a conservative to a first mutation. "Conservative" in this context means a similar amino acid in terms of the amino acid characteristics. If, for example, a mutation leads at a specific position to a substitution of a non-aliphatic amino acid residue (e.g. Ser) with an aliphatic amino acid residue (e.g. Leu) then a substitution at the same position with a different aliphatic amino acid (e.g. Ile or Val) is referred to as a conservative mutation. Further amino acid characteristics include size of the residue, hydrophobicity, polarity, charge, pK-value, and other amino acid characteristics known in the art. Accordingly, a conservative substitution may include substitution such as basic for basic, acidic for acidic, polar for polar etc. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" Comput. Appl Biosci. 9: 745-756; Taylor W. R. (1986) "The classification of amino acid conservation" J. Theor. Biol. 119; 205-218). Conservative substitutions may be made, for example, according to the table below which describes a generally accepted Venn diagram grouping of amino acids.

TABLE 2

| Venn Diagram Grouping of amino acids | | | |
|---|---|---|---|
| Characteristic | Set | Characteristic | Sub-set |
| Hydrophobic | F W Y H K M I L V A G C | Aromatic Aliphatic | F W Y H I L V |
| Polar | W Y H K R E D C S T N Q | Charged Positive | H K R E D H K R |
| | | Charged Negative | E D |
| Small | V C A G S P T N D | Tiny | A G S |

Referring to the Venn diagram of TABLE 2, variation in sequence identity with SEQ ID NOS. 13-16 (outside of SEQ ID NOS. 1-6, and optionally 7-12) may be by way of substitution of hydrophobic amino acid for another hydrophobic amino acid; aromatic aliphatic amino acid for another aromatic aliphatic amino acid; polar amino acid for another polar amino acid; charged positive amino acid for another charged positive amino acid; charged negative amino acid for another charged negative amino acid; small amino acid for another small amino acid; tiny amino acid for another tiny amino acid.

Mutation analysis of PD-1 showed substitution of amino acids L128A, P130A, I134A and K78A of PD-1 did not significantly affect hAb-10D3 binding to PD-1. Mutations E136A showed lower affinity but anti-PD-1 was still able to bind. I126A was required for antibody binding. When conducting the same study on an anti-PD-1 antibody by Merck (CAT#71120), substitutions at each of 1126, P130, 1134, E136, and K178 with alanine significant decreased binding to the Merck antibody. Replacement of L128 with alanine completed abolished PD-1 binding to the Merck antibody, which confirms different amino acids of human PD-1 are required in PD-1 binding. FIG. 6 summarizes results of the study. Furthermore, this study suggest the corresponding positions on the anti-PD-1 antibody can be mutated without loss of binding.

Preferably, the antibody or antibody fragment binds human PD-1 when human PD-1 has one or more mutations selected from the group consisting of L128A, P130A, I134A, E136A, and K78A Referring back to SEQ ID NOS. 1-6, the invention can be defined as a set of CDR regions with anti-PD-1 binding activity; however, in preferred embodiments the CDR peptides (each corresponding to a single CDR) are joined to form an anti-PD-1 antibody having a variable region for specific binding to a PD-1 epitope. Again, the antibody variable region can be present in, for example, a complete antibody, an antibody fragment (e.g. F(ab), $F(ab')_2$, scFv, minibody, tetrabody and others) or a recombinant derivative of an antibody or antibody fragment.

The term "antibody" describes an isolated immunoglobulin, whether natural or partly or wholly synthetically produced. Thus, anti-PD-1 antibodies of the present invention, in some embodiments, include any polypeptide or protein having a binding domain which is, or is substantially identical to the set of CDRs within an antibody variable region described herein that is specific for binding to a PD-1 epitope (e.g., at least about 80% identical, at least about 85% identical, at least about 90% identical, at least about 95% identical, or at least 99% identical to those herein).

In some embodiments, different antibody regions are illustrated by reference to IgG, which contains four amino acid chains—two longer length heavy chains and two shorter light chains that are inter-connected by disulfide bonds. The heavy and light chains each contain a constant region and a variable region. A heavy chain is comprised of a heavy chain variable region and a heavy chain constant region. A light chain is comprised of a light chain variable region and a light chain constant region. In some embodiments, there are three hypervariable regions within the variable regions that are responsible for antigen specificity. In some embodiments, the hypervariable regions are referred to as complementarity determining regions (CDR) and are interposed between more conserved flanking regions referred to as framework regions (FW). In various embodiments, the variable regions of the heavy and light chains contain a binding domain that interacts with an antigen.

In some aspects, the antibody variable region is present in a recombinant derivative. Examples of recombinant derivatives include single-chain antibodies, diabody, triabody, tetrabody, and miniantibody. In some embodiments, an anti-PD-1 antibody also contains one or more variable regions recognizing the same or different epitopes.

As already introduced, the CDRs of the hAb-10D3 cone originated from murine; however, hAb10D3 is a humanized antibody. As such, the anti-PD-1 antibody may be a chimeric antibody or a humanized antibody. A chimeric antibody is a monoclonal antibody constructed from variable regions derived from a different organism from the constant regions. For example, a chimeric antibody can contain variable regions from a murine source and constant regions derived from the intended host source (e.g., human). To this end, the anti-PD-1 chimeric antibodies can be formed by insertion of variable light and heavy genes from the rodent (e.g., mouse) antibody, which incorporate SEQ ID NOS. 1-6 into mammalian expression vectors which contain the appropriate human light chain and heavy chain constant domain coding regions, respectively. These heavy and light chain "chimeric" expression vectors are then cotransfected into a recipient cell line and subjected to known cell culture techniques, resulting in production of both the light and heavy chains of a chimeric antibody. Such chimeric antibodies have historically been shown to have the binding capacity of the original rodent monoclonal while significantly reducing immunogenicity problems upon host administration.

Humanized antibodies are well known in the art as antibodies from non-human species whose protein sequences have been modified to increase their similarity to antibody variants produced naturally in humans. In particular, the process of "humanization" is usually applied to monoclonal antibodies developed for administration to humans (for example, antibodies developed as anti-cancer drugs). Humanization can be necessary when the process of developing a specific antibody involves generation in a non-human immune system (such as that in rat/mouse). The protein sequences of antibodies produced in this way are partially distinct from homologous antibodies occurring naturally in humans, and are therefore potentially immunogenic when administered to human patients. For completeness, humanized antibodies are distinct from chimeric antibodies. The latter also have their protein sequences made more similar to human antibodies, but carry a larger stretch of non-human protein. Thus while CDRs 1-6 may be presented in murine form or in other mammalian form, use as a therapeutic is improved through humanization. To this end, the CDRs of SEQ ID NOS. 1-6 have been humanized to for use in pharmaceutical formulations. Techniques for humanization are well known in the art to which the invention belongs. In furtherance of this, humanizing of one or more polypeptides provided herein can done by among others, "reshaping," "hyperchimerization," "CDR grafting," "veneering," and "SDR grafting."

The anti-PD-1 antibodies may contain additional components including, but not limited to, components other than variable regions or additional variable regions that provide, or help provide, useful and/or additional activities. Useful activities include, for example, antibody effector functions such as antibody-dependent cellular cytoxicity, phagocytosis, complement-dependent cytoxicity, and half-life/clearance rate. In some embodiments, antibody effector functions are mediated by different host components, such as Fcγ receptors, neonatal Fc receptor (FcRn), and C1q. In various embodiments, different types of antibody components or alterations are used to enhance effector functions. Examples of useful components or alternations include the use of non-fucosylated oligosaccharides, amino acids altered to have increased stability (e.g. an IgG4 S228P mutation), amino acids with enhanced binding to FcRn, amino acid alterations with enhanced binding to a Fcγ receptor, and amino acid alterations with decreased binding affinity to a Fcγ receptor (e.g. an IgG1 D265A mutation).

The anti-PD-1 antibody can contains an Fc constant domain that is modified to minimize antibody dependent cell-mediated cytotoxicity, Fc gamma receptor binding, and/or complement-mediated cytotoxicity. In some embodiments, an anti-PD-1 antibody targeting the PD-L1-blocking region, a PD-L2-blocking region, a PD-L1-non-blocking region, or a PD-L2-non-blocking target region, as described herein, is contained within a bispecific antibody. In various embodiments the bispecific antibody contains an Fc or modified Fc domain that is capable of mediating antibody effector functions. In some embodiments, the bispecific antibodies are bivalent, trivalent, or tetravalent.

The anti-PD-1 antibody can contain additional components to alter the physiochemical properties of the protein, providing pharmacological advantages. For example, the attachment of polyethylene glycol ("PEG") to molecules, in some embodiments, improves safety by reducing toxicity and increasing efficiency of the molecules when used as therapeutics. Physiochemical alterations include, but are not limited to, changes in conformation, electrostatic binding, and hydrophobicity which can work together to increase systemic retention of a therapeutic agent. Additionally, by increasing the molecular weight of an anti-PD-1 antibody by attaching a PEG moiety, pharmacological advantages may include extended circulating life, increased stability, and enhanced protection from host proteases. PEG attachment can also influence binding affinity of the therapeutic moiety to cell receptors. PEG is a non-ionic polymer composed of repeating units (—O—CH$_2$—CH$_2$—) to make a range of molecular weight polymers from 400 to greater than 15,000 (e.g., PEG polymers with molecular weights of up to 400,000 are commercially available).

C. Nucleic Acids

Nucleic acid sequences encoding the anti-PD-1 polypeptide sequences, which include any of SEQ ID NOS. 1-16 are also provided. Recombinant nucleic acids encoding anti-PD-1 antibodies are particularly useful for expression in a host cell that in effect serves as a factory for the anti-PD-1 antibodies. In various embodiments, nucleic acids are isolated when purified away from other cellular components or other contaminants (e.g. other nucleic acids or proteins present in the cell) by standard techniques including, including alkaline/SDS treatment, CsCl banding, column chromatography, agarose gel electrophoresis and others well-known in the art. See e.g., F. Ausubel, et al., ed. (1987) Current Protocols in Molecular Biology, Greene Publishing and Wiley Interscience, New York. In various embodiments, a nucleic acid is, for example, DNA or RNA and may or may not contain intronic sequences. In a preferred embodiment, the nucleic acid is a cDNA molecule. In various embodiments, a recombinant nucleic acid provides a recombinant gene encoding the anti-PD-1 antibody that exists autonomously from a host cell genome or as part of the host cell genome.

In some embodiments, a recombinant gene contains nucleic acids encoding a protein along with regulatory elements for protein expression. Generally, the regulatory elements that are present in a recombinant gene include a transcriptional promoter, a ribosome binding site, a terminator, and an optionally present operator. A promoter is defined as a DNA sequence that directs RNA polymerase to bind to DNA and initiate RNA synthesis. A strong promoter is one, which causes mRNAs to be initiated at high frequency. A preferred element for processing in eukaryotic cells is a polyadenylation signal. Antibody associated introns may also be present. The degeneracy of the genetic code is such that, for all but two amino acids, more than a single codon encodes a particular amino acid. This allows for the construction of synthetic DNA that encodes a protein where the nucleotide sequence of the synthetic DNA differs significantly from the nucleotide sequences disclosed herein, but still encodes such a protein. Such synthetic DNAs are intended to be within the scope of the present invention.

If it is desired to express DNAs in a particular host cell or organism, the codon usage of such DNAs can be adjusted to maximize expression of a protein. One approach is to choose codons that reflect the codon usage of that particular host. Alternative codons which code for the identical amino acid are shown in TABLE 3, which naturally can be converted to cDNA molecules by replacing U—uracil with T—thymidine.

TABLE 3

| Codons Encoding Amino Acids | | | |
|---|---|---|---|
| Alanine | Ala | A | GCA, GCC, GCG, GCU |
| Cysteine | Cys | C | UGC, UGU |
| Aspartic Acid | Asp | D | GAC, GAU |
| Glutamic Acid | Glu | E | GAA, GAG |
| Phenylalanine | Phe | F | UUC, UUU |
| Glycine | Gly | G | GGA, GGC, GGG, GGU |
| Histidine | His | H | CAC, CAU |
| Isoleucine | Ile | I | AUA, AUC, AUU |
| Lysine | Lys | K | AAA, AAG |
| Leucine | Leu | L | UUA, UUG, CUA, CUC, CUG, CUU |
| Methionine | Met | M | AUG |
| Asparagine | Asn | N | AAC, AAU |
| Proline | Pro | P | CCA, CCC, CCG, CCU |
| Glutamine | Gln | Q | CAA, CAG |
| Arginine | Arg | R | AGA, AGG, CGA, CGC, CGG, CGU |
| Serine | Ser | S | AGC, AGU, UCA, UCC, UCG, UCU |
| Threonine | Thr | T | ACA, ACC, ACG, ACU |
| Valine | Val | V | GUA, GUC, GUG, GUU |
| Tryptophan | Trp | W | UGG |
| Tyrosine | Tyr | Y | UAC, UAU |

Expression of a recombinant gene in a cell can be facilitated using an expression vector. Expression vectors are defined herein as DNA sequences that are required for the transcription of cloned DNA and the translation of their mRNAs in an appropriate host. In various embodiments, such vectors are used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. Preferably, the expression vector, in addition to a recombinant gene, also contains an origin of replication for autonomous replication in a host cell, a selectable marker, a limited number of useful restriction enzyme sites, and a potential for high copy number.

In some embodiments, expression vectors include, but are not limited to, cloning vectors, modified cloning vectors, specifically designed plasmids or viruses. Such expression vectors, including mammalian, bacterial, fungal (e.g., Pichia), and insect cell expression vectors, are commercially available. In some embodiments, nucleic acids encoding an antibody may be integrated into the host chromosome using techniques well known in the art.

A nucleic acid having one or more recombinant genes encoding for either or both of an anti-PD-1 antibody a variable heavy chain region and variable light chain region can be used to produce a complete binding protein binding to an identified target region or a component of the binding protein. In some embodiments, a complete binding protein is provided, for example, using a single gene to encode a single chain protein containing a variable heavy chain region and variable light chain region, such as a scFv, or using multiple recombinant regions to, for example, produce both a variable heavy chain region and variable light chain region. In some embodiments, a region of a binding protein is produced, for example, by producing a polypeptide containing the variable heavy chain region and variable light chain. Nonlimiting examples of nucleic acid sequences include SEQ ID NO. 18 (reverse translated heavy chain F(ab)) and SEQ. ID NO. 19 (reverse translated light chain F(ab))

E. Pharmaceutical Formulations

The anti-PD-1 antibodies can be provided alone or as a pharmaceutical composition or a medicament, preferably for human. To this end, the compounds can be made into various pharmaceutical dosage forms according to a preventive or therapeutic purpose. Examples of pharmaceutical dosage forms are oral preparations, injections, suppositories, ointments, plasters and so on. Such preparations can be formulated in a manner already known and conventional to those skilled in the art to which the invention belongs.

The amount of the anti-PD-1 antibody to be incorporated into each of the unit dosage forms may vary with the medical condition of the patient or with the type of the preparations. The preferable amount per dosage unit is about 1 to about 1,000 mg for oral preparations, about 0.1 to about 500 mg for injections, or about 5 to about 1,000 mg for suppositories. The dosage per day can be variable with the symptoms, body weight, age, sex and other factors of the patient, but usually ranges from about 0.1 to about 5,000 mg, preferably from about 1 to about 1,000 mg for human adult per day. The preparation is preferably administered in a single dose or in two to four divided doses.

For the formulation of solid preparations for oral administration, an excipient and, when required, a binder, disintegrator, lubricant, coloring agent, corrigent, flavor, etc. are added to the anti-PD-1 formulation, and then a preparation is formulated in a conventional way as tablets, coated tablets, granules, powders, capsules or others. Such additives are those already known in the art, and useful examples are excipients such as lactose, sucrose, sodium chloride, glucose, starch, calcium carbonate, kaolin, microcrystalline cellulose and silicic acid; binders such as water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate and polyvinyl pyrrolidone; disintegrators such as dried starch, sodium alginate, agar powder, sodium hydrogencarbonate, calcium carbonate, sodium lauryl sulfate, stearic acid monoglyceride and lactose; lubricants such as purified talc, stearic acid salt, borax and polyethylene glycol; corrigents such as sucrose, bitter orange peel, citric acid and tartaric acid, etc.

As a nonlimiting embodiment, a tablet can be prepared in a convention manner staring from the following components of proportions indicated below.

| | |
|---|---|
| hAg-10D3 | 100 mg |
| Lactose | 47 mg |
| Corn starch | 50 mg |
| Microcrystalline cellulose | 65 mg |
| Talc | 2 mg |
| Magnesium stearate | 2 mg |
| Ethyl cellulose | 30 mg |
| Unsaturated fatty acid glyceride | 4 mg |
| Per tablet | 300 mg |

As a nonlimiting embodiment granules can be prepared in a convention manner using the following components of the proportions indicated below.

| | |
|---|---|
| hAg-10D3 | 200 mg |
| Mannitol | 540 mg |
| Corn starch | 100 mg |
| Crystalline cellulose | 100 mg |
| Hydroxypropyl cellulose | 50 mg |
| Talc | 10 mg |
| Per wrapper | 1000 mg |

As a nonlimiting embodiment capsules can be prepared in a convention manner using the following components of the proportions indicated below.

| | |
|---|---|
| hAg-10D3 | 300 mg |
| Lactose | 50 mg |
| Corn starch | 47 mg |
| Crystalline cellulose | 50 mg |
| Hydroxypropyl cellulose | 50 mg |
| Talc | 2 mg |
| Magnesium stearate | 1 mg |
| Per capsule | 500 mg |

For the formulation of liquid preparations for oral administration, a corrigent, buffer, stabilizer, flavor, etc. can be added to the compound, and the mixture can be formulated in a conventional way into an oral liquid preparation, syrup, elixir or the like. Examples of useful corrigents are those exemplified above. Examples of buffers are sodium citrate, etc. Examples of stabilizers are tragacanth, gum arabic, gelatin, etc. As a nonlimiting embodiment syrups can be prepared in a convention manner using the following components of the proportions indicated below.

| | |
|---|---|
| hAg-10D3 | 500 mg |
| Sucrose | 30 mg |
| Gelatin solution | Suitable amount |
| Flavoring/Coloring | Suitable amount |
| Purified water | q.s |
| Total | 500 mL |

Injections can be prepared as a subcutaneous, intramuscular or intravenous injection in a conventional way by adding to the anti-PD-1 antibody a pH adjusting agent, buffer, stabilizer, isotonic agent, local anesthetic, etc. Examples of pH adjusting agents and buffers are sodium citrate, sodium acetate, sodium phosphate, etc. Examples of stabilizers are sodium pyrosulfite, EDTA, thioglycolic acid, thiolactic acid, etc. Examples of local anesthetics are procaine hydrochloride, lidocaine hydrochloride, etc. Examples of isotonic agents are sodium chloride, glucose, etc. As a nonlimiting embodiment, injection formulations can be prepared in a convention manner using the following components of the proportions indicated below.

| | |
|---|---|
| hAb-10D3 | 50 mg |
| pH buffered saline | q.s. |
| Total per ampule | 1 mL |

Suppositories can be prepared in a usual manner by adding to the anti-PD-1 antibody a pharmaceutically acceptable carrier already known in the art, such as polyethylene glycols, lanolin, cacao fat and oil, fatty acid triglycerides and, if desired, a surfactant such as TWEEN. As a nonlimiting embodiment, suppositories can be prepared in a convention manner using the following components of the proportions indicated below.

| | |
|---|---|
| Compound 2a23 | 100 mg |
| Triglyceride of saturated fatty acid | 1400 mg |
| Total per suppository | 1500 mg |

For the preparation of ointments, a base, a stabilizer, a humectant, a preservative and the like commonly used in the art are used as required. These additives together with the anti-PD-1 antibody are formulated into ointments by conventional methods. Useful examples of the base include, for example, liquid paraffin, white petrolatum, bleached beeswax, octyl dodecyl alcohol, paraffin, etc. As preservatives, there can be mentioned methyl para-hydroxybenzoate, ethyl para-hydroxybenzoate, para-hydroxy propyl benzoate, etc.

For the preparation of plasters, ointment, cream, gel or paste the compound is applied to a substrate commonly employed in the art in a conventional manner. Suitable examples of substrates are woven or non-woven fabrics of cotton, rayon, chemical fibers or the like and films or foamed sheets of soft vinyl chloride, polyethylene, polyurethane or the like.

F. Treatment with Anti-PD-1 Antibodies

The anti-PD-1 antibodies, namely, hAb-10D3, and its variations herein may be used therapeutically to interfere with the interaction between PD-1 and PD-L1 and/or PD-1 and PD-L2. Administration of the anti-PD-1 antibody, alone or in combination with additional substances, will take the form of a composition that includes a pharmaceutically acceptable carrier. In some embodiments, the anti-PD-1 antibodies as described herein are used under circumstances where an enhanced or augmented immune response, particularly an enhanced T cell response, is desired via attenuating the inhibitory signaling mediated by PD-1. A downregulation of PD-1 activity is especially desirable to treat microbial infections (e.g., bacteria, fungi, viruses) and cancer. In some embodiments, a blockade of PD-1/PD-L1 or PD-1/PD-L2 interaction using an anti-PD-1 antibody leads to enhanced T cell responses, consistent with a downregulatory role in the PD-1 pathway. Thus, the methods of enhancing the cellular immune response in a subject are provided, preferably a human subject, which includes administering an anti-PD-1 antibody, or pharmaceutical composition thereof. The enhancement of cellular immunity is a result of therapeutic and/or prophylactic treatment of administering the anti-PD-1 antibody.

In some embodiments, the anti-PD-1 antibodies are used as part of a prophylactic treatment method. In some embodiments, an anti-PD-1 antibody is used as an adjuvant in a vaccination regime to immunize a subject, preferably a human subject, against a specific disease, including but not limited to a microbial infection or a cancer. The vaccination regimen can be used on the general population or a subset of the general population. A subset of the general population is persons at an increased risk of developing a microbial infection or cancer.

A composition, which includes a vaccine (either a prophylactic or therapeutic vaccine) and the anti-PD-1 antibody, in some embodiments, is administered with either a single administration or within the confines of a prime/boost-type vaccine regimen. Preferably, the vaccine priming and boosting administrations are different in order to evade any host immunity directed against the first delivered vaccine, especially if that vaccine is delivered as part of a 'non-self' recombinant vehicle, such as a recombinant non-viral (e.g., plasmid) or viral (e.g., adenovirus, AAV, etc.) vehicle. Thus, the compositions having one or more anti-PD-1 antibodies described herein in combination with one or more vaccines for prophylactic immunization and/or therapeutic treatment of a subject and the administration of such a vaccine composition to a subject is provided. Alternatively, the anti-PD-1 antibody and the vaccine can be separately formulated and either co-administered or administered at different time points. In some embodiments, a vaccine comprises a cell based vaccine. In various embodiments, a cell-based vaccine having an anti-PD-1 antibody is administered outside of the host, prior to cellular therapy as a method of "priming." In various embodiments, a cell-based vaccine comprising a PD-1 antibody is administered outside of the host, prior to cellular therapy as a method of "priming."

The anti-PD-1 antibody can be used as a therapeutic agent to enhance the cellular immune response of a patient. In some embodiments, the anti-PD-1 antibody is administered alone or in combination with additional therapeutic agents. Thus, the present invention is further drawn to compositions having one or more anti-PD-1 antibodies described herein in combination with additional therapeutic agents (e.g., therapeutic vaccine, anti-microbial agents, chemotherapeutic substances, antibodies against other therapeutic targets). When administered in combination with additional therapeutic agents, each component (i.e., the anti-PD-1 antibody and the additional therapeutic agent), in some embodiments, is present within a single composition and administered in a single dose. Alternatively, each component, in some embodiments, is separately formulated and either administered to the subject contemporaneously or at different time points.

The anti-PD-1 antibody can also be used in a method of treating a patient with a microbial infection including the step of administering to the patient an effective amount of an anti-PD-1 antibody as described herein or a pharmaceutical composition thereof. In some embodiments, the anti-PD-1 antibody is administered alone or in combination with additional anti-microbial substances. In various embodiments, administration of an anti-PD-1 antibody as described herein is part of a therapeutic regime to treat patients already infected with a microbial pathogen (therapeutic treatment). Alternatively, an anti-PD-1 antibody, in some embodiments, is used as part of prophylactic method to help protect an individual against becoming infected (i.e., a vaccination based method). For example, an anti-PD-1 antibody is used as an adjuvant.

Microbial infections, in some embodiments, are capable of being treated by administering an anti-PD-1 antibody described herein. In some embodiments, a microbial infection is a persistent infection. Acute infections are generally resolved from the body by the immune system relatively quickly, while persistent infections may last for months, years, or even a lifetime. Thus, persistent infections are the result of an infectious microbial agent (e.g., virus, bacterium, parasite, mycoplasm, fungus) that is not effectively cleared or eliminated from the host even after the induction of an immune response. Persistent infections may be chronic infections and/or latent infections. These infections may recur, involving stages of silent and productive infection without cell killing or even producing excessive damage to host cells.

The anti-PD-1 antibodies described herein that bind to PD-1 can be used as either part of a therapeutic regime to treat a subject, preferably a human subject, suffering from cancer or part of a prophylactic region to be administered to individuals susceptible to developing cancer. These methods include a step of administering to the patient or individual an effective amount of an anti-PD-1 antibody, or composition thereof. In some embodiments, the anti-PD-1 antibody is administered alone as a monotherapy or in combination with additional anti-cancer substances. As a non-limiting example, an anti-PD-1 antibody described herein is combined with an anti-cancer vaccine to act as an adjuvant in either a prophylactic or therapeutic regime using methods similar to that described above for microbial infections. Thus, in one embodiment, the invention provides a method of inhibiting growth of tumor cells in a subject, preferably a human subject, comprising administering to the subject a therapeutically effective amount of an anti-PD-1 antibody described herein.

Cancer treatment and/or prevention methods include the treatment and/or prevention of one or more common types of cancers diagnosed with high frequency (e.g., cancers of the blood, breast, prostate, colon and rectal, lung, prostate, brain, and skin), especially those typically responsive to immunotherapy. Thus, methods of blocking the inhibitory signal from PD-1 by administering an anti-PD-1 antibody described herein for the treatment of one or more cancers is included as part of the present invention (e.g., ovarian cancer; cancers of non-lymphoid parenchymal organs including the heart, placenta, skeletal muscle and lung; breast cancer; cancers of the head and neck including various lymphomas, such as mantle cell lymphoma, non-Hodgkins B cell lymphoma, PTCL, adenoma, squamous cell carcinoma, laryngeal carcinoma, salivary carcinoma, thymomas and thymic carcinoma; leukemia; cancers of the retina; cancers of the esophagus; multiple myeloma; melanoma; colorectal cancer; lung cancer; cervical cancer; endometrium carcinoma; gallbladder cancer; liver cancer; thyroid follicular cancer; gastric cancer; non-small cell lung carcinoma; glioma; urotheial cancer; bladder cancer; prostate cancer; renal cell cancer; infiltrating ductal carcinoma; and glioblastoma multiform).

An anti-PD-1 antibody of the present invention can be combined with an immunogenic agent, such as cancerous cells, purified tumor antigens (including recombinant proteins, peptides and carbohydrate molecules), modified immune cells, such as chimeric antigen receptor (CAR) T cells, and cells transfected with genes encoding immune stimulating cytokines.

Anti-PD-1 antibodies of the present invention can be combined with standard cancer treatments. For example, in some embodiments, administration of the anti-PD-1 antibodies is combined with chemotherapeutic regimes. In these instances, in some embodiments, it is possible to reduce the dose of chemotherapeutic reagent administered. The scientific rationale behind the combined use of the anti-PD-1 antibodies and chemotherapy is that cell death resulting from cytotoxic action of most chemotherapeutic compounds should result in increased levels of tumor antigen in the antigen presentation pathway. Other combination therapies that may be effective when combined with the PD-L1 inhibitory signal are radiation, surgery, hormone deprivation, and antibodies targeting other immune checkpoint pathways (e.g. anti-CTLA4 antibodies). Each of these protocols creates a source of tumor antigen in the host. Angiogenesis inhibitors may also be combined with PD-L1 blockade. Inhibition of angiogenesis leads to tumor cell death which may feed tumor antigen into host antigen presentation pathways.

Reference to a substance having "anti-cancer" activity or an "anti-cancer substance" indicates a substance that inhibits the proliferation of cancerous cells, including substances that inhibit the growth of tumors. Substances that display anti-cancer activity include, without limitation, substances having cytotoxic chemotherapeutic effects and anti-cancer vaccines.

Anti-PD-1 antibodies, and compositions thereof, can be administered to the host subject using one or more of the following routes: intravenous (IV), intramuscular (IM), and subcutaneous (SC), with IV administration being the norm within the art of therapeutic antibody administration. In some embodiments, these compositions are utilized in a regimen which may include a monovalent or multivalent composition and various combined modality applications. Therefore, these formulations, in some embodiments are administered as separate or multiple doses (i.e., administration of the anti-PD-1 antibody at staggered times by maintaining the sterile condition of the formulation through the treatment regime).

The dosage regimen utilizing the anti-PD-1 antibodies of the present invention can be selected in accordance with a variety of factors including type, species, age, weight, sex and medical condition of the patient; the severity of the condition to be treated; the route of administration; the renal, hepatic and cardiovascular function of the patient; and the particular anti-PD-1 antibody thereof employed. In some embodiments, the dosing frequency varies depending upon the effectiveness and stability of the compound. Examples of dosing frequencies include daily, biweekly, weekly, monthly and bimonthly. A physician or veterinarian of ordinary skill can readily determine and prescribe the effective therapeutic and/or prophylactic amount of the anti-PD-1 antibody. Optimal precision in achieving concentrations of anti-PD-1 antibodies within the range that yields efficacy without toxicity requires a regimen based on the kinetics of the protein's availability to target sites. This involves a consideration of the distribution, equilibrium, and elimination of a drug. It is expected that an effective dose range should be about 0.1 mg/kg to 20 mg/kg, or 0.5 mg/kg to 5 mg/kg.

The anti-PD-1 antibodies described herein can be used alone at appropriate dosages. In some embodiments, co-administration or sequential administration of other agents are desirable. In some embodiments, the individual components of a combination treatment regime are administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the anti-PD-1 antibodies of this invention with other agents includes in principle any combination with any pharmaceutical composition for treatment of a specific disease state, including but not limited to microbial infections and cancer. When an anti-PD-1 antibody described herein is used in combination with an additional therapeutic agent, the dose of each component may be either the same as or different from the dose when the component is used alone.

EXAMPLES

Examples are provided below further illustrating different features of the present invention. The examples also illustrate useful methodology for practicing the invention. The examples do not limit the scope of the claimed invention

Example 1

Production of Anti-PD-1 Antibodies

Five BALB/C mice were immunized subcutaneously with 50 µg of purified recombinant human PD-1 peptide in Complete Freund's Adjuvant (CFA) followed by four subsequent doses of 25 µg in Incomplete Freund's Adjuvant (IFA). Pre-bleed and test bleed samples were collected through the tail vein into microcentrifuge tubes, allowed to clot, and centrifuged to collect serum. Following the centrifuge, an ELISA was run against the antigen and the serum was stored in microcentrifuge tubes at −20° C. To perform the ELISA, briefly, microtiter plates were coated with purified recombinant PD-1 fusion protein from transfected HEK293 cells at 1-2 µg/ml in PBS, 100 µl/wells incubated at 4° C. overnight and then blocked with 250 µl/well of 3% BSA in PBS. Dilutions of sera from PD-1-immunized mice were added to each well and incubated for 1-2 hours at ambient temperature. The plates were washed with PBS/Tween (0.05%) and then incubated with a goat-anti-mouse IgG polyclonal antibody conjugated with horseradish peroxidase (HRP) for 1 hour at room temperature. After washing, the plates were developed with TMB substrate (KPL product #52-00-01) and analyzed by spectrophotometer using an OD 650. Mice that developed the highest titers of anti-PD-1 antibodies were used for fusions. Fusions were performed as described below and hybridoma supernatants were tested for anti-PD-1 activity by ELISA.

To create hybridomas the spleen was collected post euthanasia at day 127 from 5 mice and the cells were fused with an immortal cell line on Day 0 using PEG based on standard protocols. These cells were cultured for about 10 days and before selection.

Clonal culture supernatants were harvested and screened against purified human PD-1 peptide for hits by ELISA as described above. The hits from ELISA were expanded and then screened for their ability to inhibit human PD-1:PD-L1 (PD-L2) interaction in a biochemical-based screen using purified, recombinant peptide. To perform the biochemical-based screen, briefly, 100 ng of PD-L1 (PD-L2) was coated onto a 96-well plate in PD-1 Assay Buffer followed by addition of 10 ng of human PD-1-Biotin with hybridoma culture supernatants. After a wash step, the amount of bound PD-1-Biotin was quantitated using Strep-HRP and HRP chemiluminescent substrate. Clone 10D3 that had maximal inhibition effect was chosen and sub-cloned and again screened against purified human PD-1 peptide by ELISA and biochemical PD-1:PD-L1 (PD-L2) interaction assay as described above. Positive sub-clones were expanded, total RNA from hybridoma was prepared and the cDNA of antibody was PCRed and sequenced using standard sequencing techniques.

Chimeric antibody of clone 10D3 was created by fusing the variable region of clone 10D3 with the constant region of human IgG1 in place of the mouse constant region and cloning the fusion product into mammalian expression using standard cloning techniques. The cloned fusion product was then transiently expressed in HEK293 cells by transfection with polyethylenimine (PEI). Briefly, suspension HEK293 cells were seeded at a density of $1 \times 10^6$ cells/ml. anti-PD-1 expressing DNA was combined with PEI in Opti-MEM and incubate for 15 minutes at room temperature. After the incubation, DNA-PEI mixture was added to cell suspension at 2 µg/ml DNA and 4 µg/ml PEI. Cultures were allowed to grow for 4 days. The chimeric antibodies were purified from HEK293 cells using protein A affinity chromatography and the antibody was characterized by ELISA and PD-1:PD-L1 (PD-L2) binding assay as described above.

Chimeric anti-PD-1 antibody was humanized using the publicly available Tool for AntiBody HUminzation (Tabhu) server (circe.med.uniromal.it/tabhu). Heavy and light chain sequences from the chimeric anti-PD-1 antibody were uploaded to the server. These sequences were BLASTed against a database of more than 2500 antibody sequences and canonical structures were calculated together with germline genes. For both the heavy and light chain sequences, the clone titled AAB24405 showed the highest homology to the chimeric anti-PD-1 antibody. Select framework residues in the Fab region of the chimeric anti-PD-1 antibody that were non-homologous to clone AAB24405 were chosen for back-mutation to the corresponding human amino acid using synthetic gene synthesis. This humanized anti-PD-1 antibody expression construct was created by fusing with constant region of human IgG4 (S228P mutant), expressed and purified as described above and prepared for further characterization.

Example 2

Figure 1B:
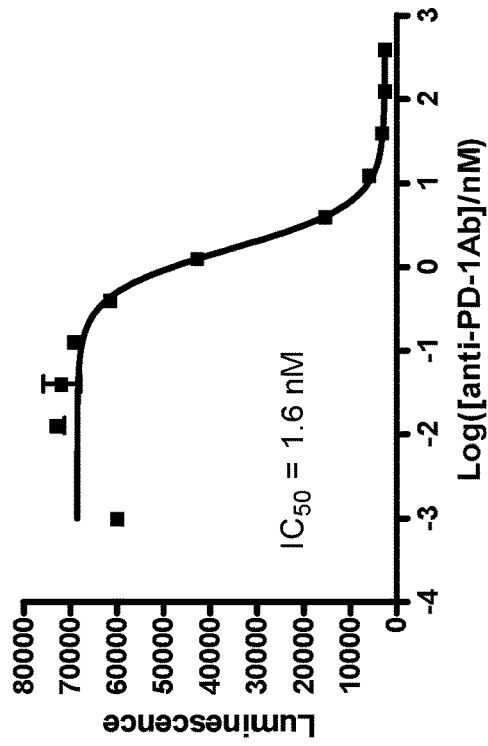

Inhibition of Human PD-1:PD-L1 Interaction 100 ng of Human PD-L1 was coated onto a 96-well plate in PD-1 Assay Buffer followed by addition of 10 ng of human PD-1-Biotin and varying amounts of hAb-10D3 anti-PD-1 neutralizing antibodies. After a wash step, the amount of bound PD-1-Biotin was quantitated using Strep-HRP and HRP chemiluminescent substrate. The results are shown in FIG. 1A, which depicts effective inhibition of PD-1:PD-L1 binding by hAb-10D3 in a dose dependent manner. FIG. 1B is a positive control for comparison using a chimeric anti-PD-1 antibody.

Example 3

Figure 2:
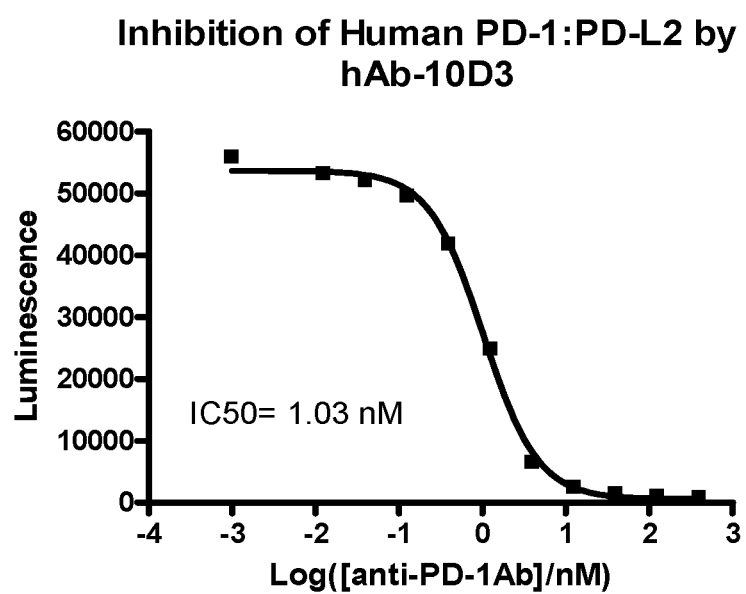
FIG. 2 is a graph depicting the inhibition of human PD-1:PD-L2 interaction with hAb-10D3 of over a series of different concentrations.

Inhibition of Human PD-1:PD-L2 Interaction 100 ng of Human PD-L2 was coated onto a 96-well plate in PD-1 Assay Buffer followed by addition of 6 ng of human PD-1-Biotin and varying amounts of hAb-10D3 anti-PD-1 neutralizing antibodies. After a wash step, the amount of bound PD-1-Biotin is quantitated using Strep-HRP and HRP chemiluminescent substrate. The results are shown in FIG. 2, which depicts effective inhibition of PD-1:PD-L2 binding by hAb-10D3 in a dose dependent manner.

Example 4

Figures 3A, 3B:
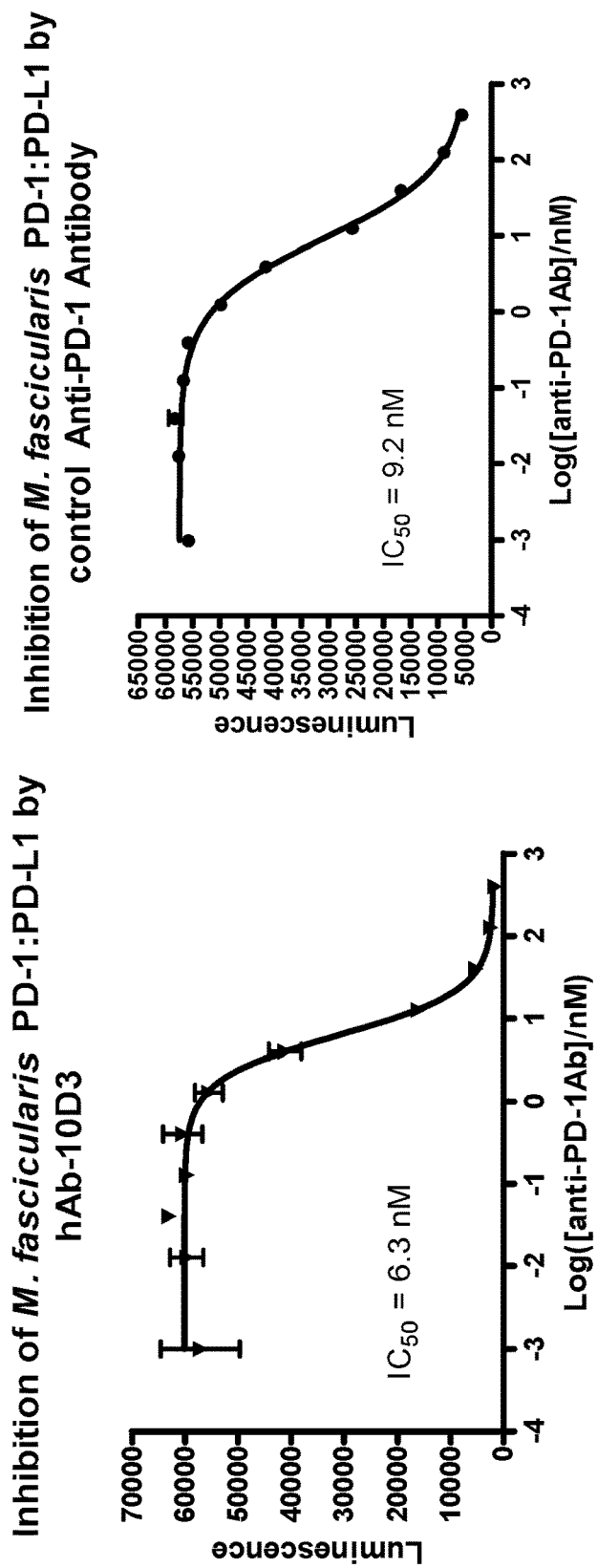
FIG. 3A and FIG. 3B is a series of graphs depicting inhibition of *M. fascicularis* PD-1:PD-L1 interaction with hAb-10D3 over a series of concentrations compared to positive control.

Inhibition of M. fascicularis PD-1:PD-L1 Interaction 100 ng M. fascicularis PD-1 was coated onto a 96-well plate in PD-1 Assay Buffer followed by addition of 40 ng of M. fascicularis PD-L1-Biotin and varying amounts of HAB-10D3 anti-PD-1 neutralizing antibodies. After a wash step, the amount of bound PD-L1-Biotin is quantitated using Strep-HRP and HRP chemiluminescent substrate. The results are shown in FIG. 3—panel A, which depicts effective inhibition of PD-1:PD-L2 binding by hAb-10D3 in a dose dependent manner. FIG. 3B is a positive control for comparison using a chimeric anti-PD-1 antibody.

Example 5

Figures 4A, 4B:
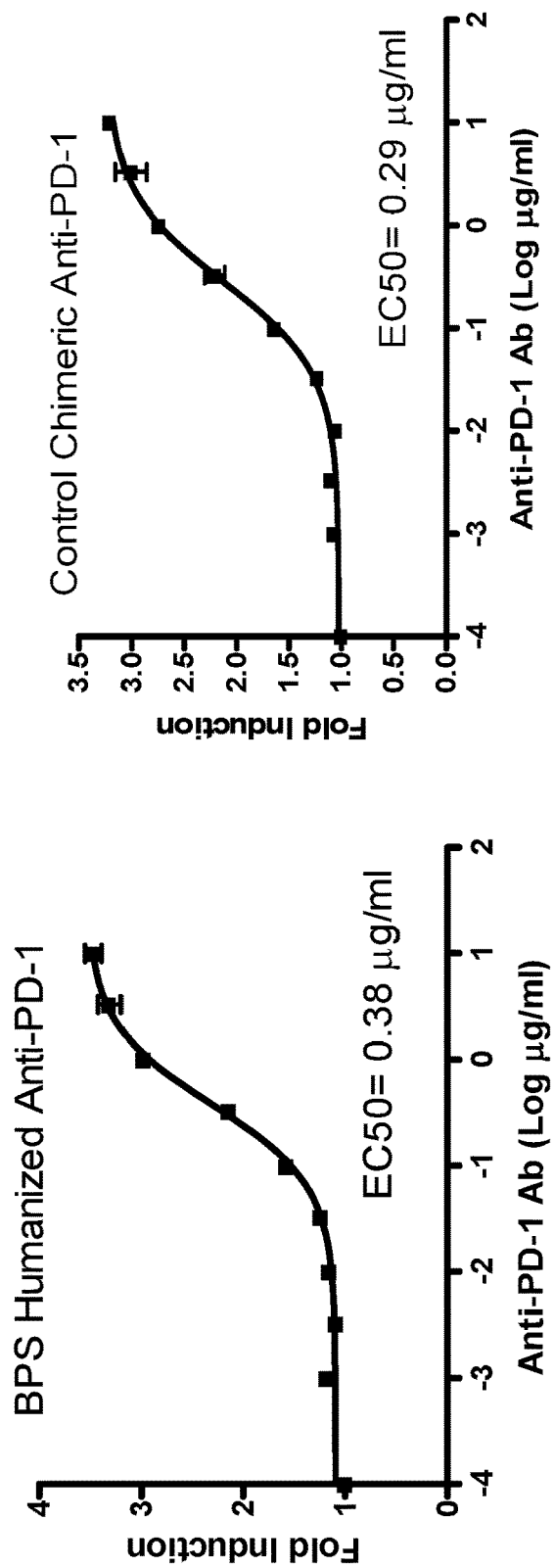
FIG. 4A and FIG. 4B are a series of graphs depicting neutralization of human PD-1 signaling with hAb-10D3 over different concentrations compared to control.

Increasing T Cell Activation Using a Humanized Anti-Human PD-1 Neutralizing Antibody HEK293 cells expressing PD-L1 were incubated with Jurkat T cells expressing NFAT luciferase reporter and PD-1. T cells were activated by CD3 cross-linking in the presence of varying amounts of anti-PD-1 antibody. The level of activation is indirectly measured by measuring luciferase activity. In this experiment, BPS hAb-10D3 anti-PD-1 neutralizing antibody (FIG. 4A) was compared to a control chimeric anti-PD-1 antibody known to inhibit PD-1 activity (FIG. 4B). In summary, hAb-10D3 inhibited PD-1 signaling with an EC50 of 0.38 µg/mL (FIG. 4A) and positive control chimeric antibody inhibited PD-1 signaling with an EC50 of 0.29 µg/mL.

Example 6

Biotin-Labeled PD-1 Mutants Binding Comparison Between Human PD-L1, Merck Anti-PD-1 Ab, and BPS hAb-10D3

Wells were coated with 100 ng of PD-L1, Merck anti-PD-1 antibody (CAT#71120) or BPS hAb-10D3 (CAT#H10D3) overnight in PBS buffer. After subsequent washing and blocking steps, 1 ng of biotinylated PD-1 or mutants in 50 µL of assay buffer were added to the coated wells. SEQ ID NO. 17 provides the base sequence from which the mutants were generated. FIG. 5 depicts SEQ ID NO. 17 showing amino acids 25-167 of human PD-1, joined to a linker sequence (bold), joined to Fc of human IgG1 (amino acids 100-330)(underlined), joined to avidin tag (italics). Points of mutation for K78A, I126A, L128A, P130A, I134A, E136A are shown in larger font. The reaction was incubated for 2 h at room temperature before adding strep-HRP, followed by chemiluminescent substrates. Luminescence was read on a chemiluminescent plate reader.

FIG. 6 provides the results. Merck anti-PD-1 antibody and BPS hAb-10D3 showed different binding profiles across the human PD-1 mutants demonstrating a difference in antibody structure and binding site.

What is claimed is:

1. An antibody or antibody fragment that binds human PD-1, the antibody or antibody fragment comprising a heavy chain variable region comprising the CDR sequences set forth in SEQ ID NOS. 1-3; and a light chain variable region comprising the CDR sequences set forth in SEQ ID NOS. 4-6.

2. The antibody or antibody fragment of claim 1, wherein the antibody or antibody fragment inhibits or reduces PD-1 binding to PD-L1, PD-L2, or PD-L1 and PD-L2.

3. The antibody or antibody fragment of claim 1, in a form of a chimeric antibody or fragment thereof.

4. The antibody or antibody fragment of claim 1, in a form of a humanized antibody or fragment thereof.

5. The antibody or antibody fragment of claim 1, which binds human PD-1 when human PD-1 comprises one or more mutations selected from the group consisting of L128A, P130A, I134A, E136A, and K78A.

6. The antibody or antibody fragment of claim 1, wherein the heavy chain variable region comprises a contact sequence selected from the group consisting of any of the contact sequences set forth in SEQ ID NOS. 7-9, optionally all three contact sequences of SEQ ID NOS. 7-9.

7. The antibody or antibody fragment of claim 1, wherein the heavy chain variable region comprises an amino acid sequence comprising at least 85% sequence identity to SEQ ID NO. 13, optionally at least 90% sequence identity to SEQ ID NO. 13.

8. The antibody or antibody fragment of claim 1, wherein the heavy chain variable region comprises the amino acid sequence set forth in SEQ ID NO. 13.

9. The antibody or antibody fragment of claim 1, wherein the light chain variable region comprises a contact sequence selected from the group consisting of any of the contact sequences set forth in SEQ ID NOS. 10-12, optionally all three contact sequences of SEQ ID NOS. 10-12.

10. The antibody or antibody fragment of claim 1, wherein the light chain variable region comprises an amino acid sequence comprising at least 85% sequence identity to SEQ ID NO. 14, optionally at least 90% sequence identity to SEQ ID NO. 14.

11. The antibody or antibody fragment of claim 1, wherein the light chain variable region comprises the amino acid sequence set forth in SEQ ID NO. 14.

12. The antibody or antibody fragment of claim 1, wherein the heavy chain variable region comprises the contact sequences set forth in SEQ ID NOS. 7-9 and the light chain variable region comprises the contact sequences set forth in SEQ ID NOS. 10-12.

13. An antibody or antibody fragment capable of binding human PD-1, comprising:
   a) a heavy chain variable region comprising at least 85% sequence identity to the amino acid sequence set forth in SEQ ID NO: 13, the heavy chain variable region further comprising three CDR sequences set forth in SEQ ID NOS. 1-3 and three contact sequences set forth in SEQ ID NOS. 7-9; and
   b) a light chain region variable region comprising at least 85% sequence identity to the amino acid sequence set forth in SEQ ID NO: 14, the light chain variable region further comprising three CDR sequences set forth in SEQ ID NOS. 4-6 and three contact sequences of SEQ ID NOS. 10-12.

14. The antibody or antibody fragment of claim 12, wherein the heavy chain variable region comprises at least 90% sequence identity to the amino acid sequence of SEQ ID NO. 13 and the light chain variable region comprises at least 90% sequence identity to the amino acid sequence of SEQ ID NO. 14.

15. The antibody or antibody fragment of claim 12, wherein the heavy chain variable region comprises the amino acid sequence of SEQ ID NO. 13 and the light chain variable region comprises the amino acid sequence of SEQ ID NO. 14.

16. The antibody or antibody fragment according to claim 1, in a pharmaceutically acceptable carrier.

17. A nucleic acid sequence encoding the antibody or antibody fragment according to claim 1.

18. A method of interfering with the interaction of PD-L1 with PD-1 comprising:
   a) providing a sample comprising PD-1;
   b) contacting the PD-1 with the antibody or antibody fragment of claim 1; and
   c) exposing the PD-1 to PD-L1.

19. A method of interfering with the interaction of PD-L2 with PD-1 comprising:
   a) providing a sample of PD-1;
   b) contacting the PD-1 with the antibody or antibody fragment of claim 1; and
   c) exposing the PD-1 to PD-L2.

20. A method of interfering with the interaction of PD-L1 and PD-L2 with PD-1 comprising:
   a) providing a sample of PD-1;
   b) contacting the PD-1 with the antibody or antibody fragment of claim 1; and
   c) exposing the PD-1 to PD-L1 and PD-L2.

21. A method of reducing PD-1 signaling in a cell, the method comprising:
   a) providing a cell expressing PD-1;
   b) contacting the cell with the antibody or antibody fragment of claim 1; and
   c) exposing the cell to PD-L1, PD-L2, or both PD-L1 and PD-L2.

* * * * *